(12) United States Patent
Imamura

(10) Patent No.: US 9,980,637 B2
(45) Date of Patent: May 29, 2018

(54) IMAGE PROCESSING APPARATUS AND IMAGE PROCESSING METHOD

(71) Applicant: CANON KABUSHIKI KAISHA, Tokyo (JP)

(72) Inventor: Hiroshi Imamura, Kyoto (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days. days.

(21) Appl. No.: 15/202,233

(22) Filed: Jul. 5, 2016

(65) Prior Publication Data

US 2017/0007113 A1 Jan. 12, 2017

(30) Foreign Application Priority Data

Jul. 7, 2015 (JP) .................................. 2015-136387

(51) Int. Cl.
*A61B 3/14* (2006.01)
*A61B 3/00* (2006.01)
*A61B 3/12* (2006.01)
*A61B 3/10* (2006.01)

(52) U.S. Cl.
CPC .......... *A61B 3/0025* (2013.01); *A61B 3/1025* (2013.01); *A61B 3/1241* (2013.01)

(58) Field of Classification Search
CPC .... A61B 3/0025; A61B 3/1025; A61B 3/1241
USPC ....................... 351/206, 205, 200
See application file for complete search history.

(56) References Cited

U.S. PATENT DOCUMENTS 8,408,704 B2 * 4/2013 Tomidokoro .......... A61B 3/102
351/205

OTHER PUBLICATIONS

N. Chapman, N. Witt, A.A. Bharath, A.V. Stanton, S.A. Thorn, A.D. Hughes, Computer Algorithms for the Automated Measurement of Retinal Arteriolar Diameters, British Journal of Ophthalmology, Jan. 2001, 88(1):74-79, BMJ Publishing Group, London, UK, 2001.
Edouard Koch, David Rosenbaum, Aurelie Brolly, José-Alain Sahel, Philippe Chaumet-Riffaud, Xavier Girerd, Florence Rossant, Michel Paques, Morphometric Analysis of Small Arteries in the Human Retina Using Adaptive Optics Imaging: Relationship with Blood Pressure and Focal Vascular Changes, Journal of Hypertension, Apr. 2014, 32(4):890-898, Lippincott Williams & Wilkins, Philadelphia, PA, 2014.

* cited by examiner

*Primary Examiner* — Tuyen Tra
(74) *Attorney, Agent, or Firm* — Canon U.S.A., Inc., IP Division

(57) ABSTRACT

An image processing apparatus includes a processing unit configured to perform, on a luminance distribution acquired in at least one direction crossing a vessel region in a fundus image of a subject's eye, a first smoothing operation for each first size and a second smoothing operation for each second size smaller than the first size; a first identifying unit configured to identify a position of a vascular wall in the fundus image on the basis of the luminance distribution obtained by performing the first smoothing operation; and a second identifying unit configured to identify positions of inner and outer boundaries of the vascular wall in the fundus image on the basis of the luminance distribution obtained by performing the second smoothing operation.

18 Claims, 17 Drawing Sheets

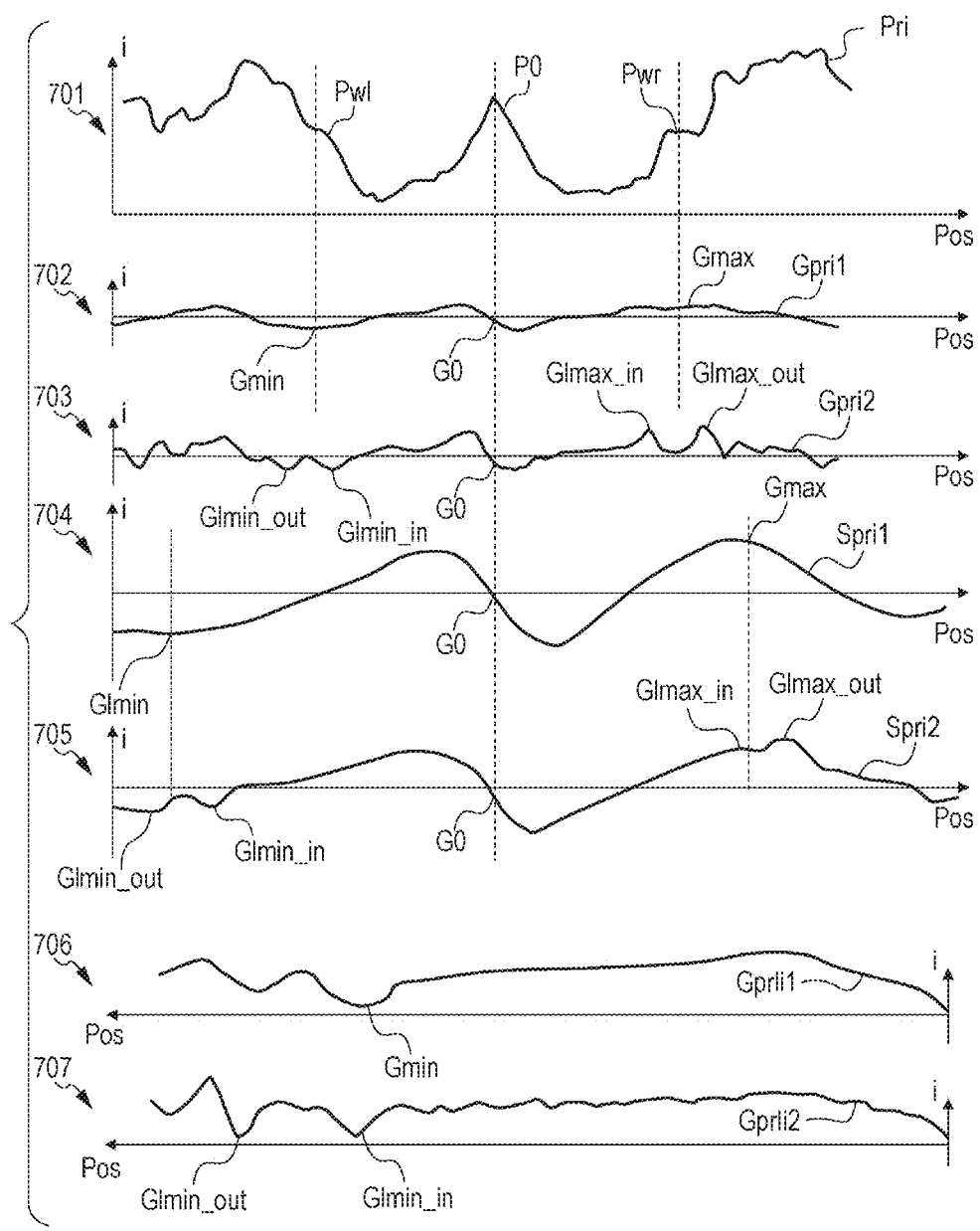

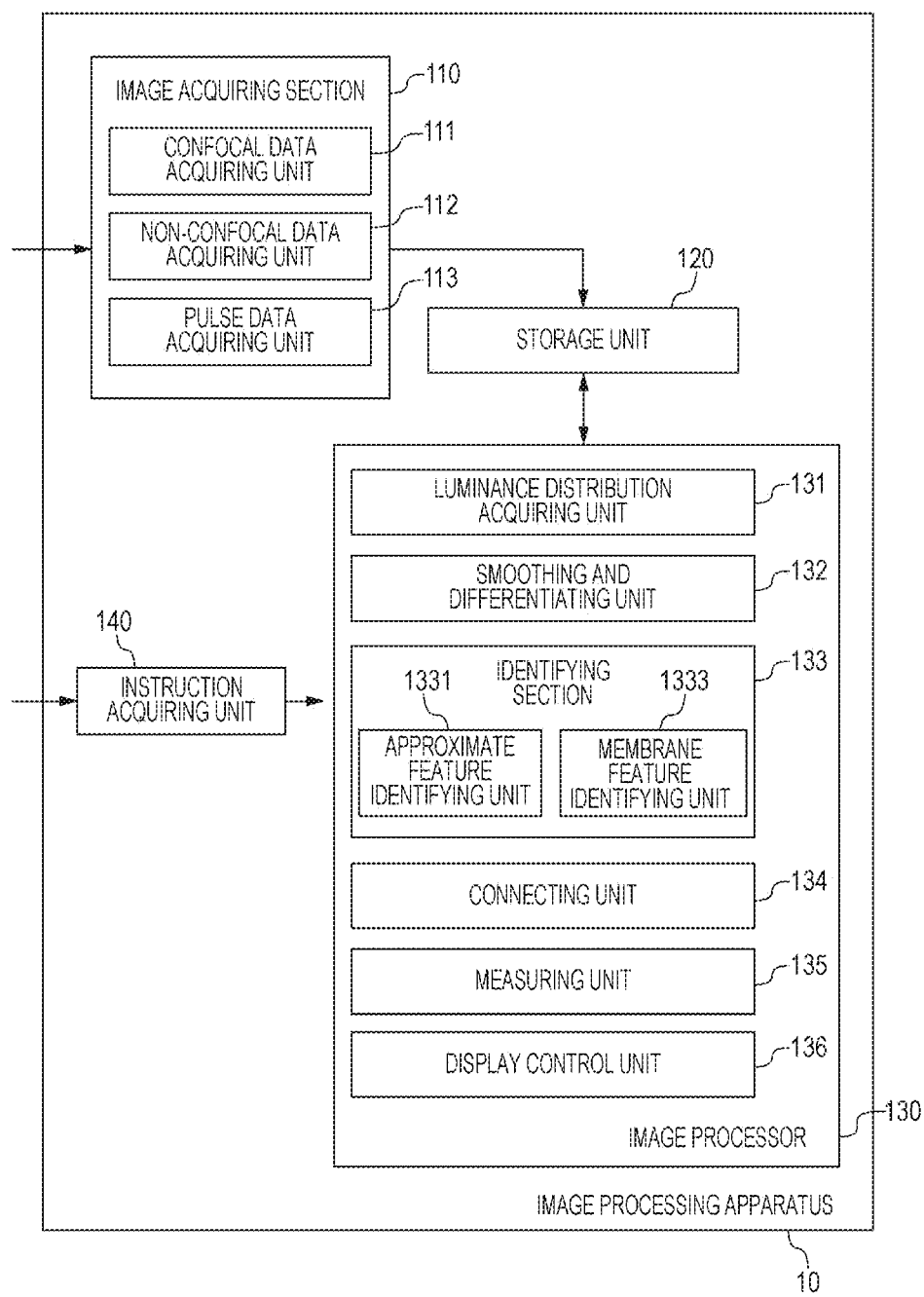

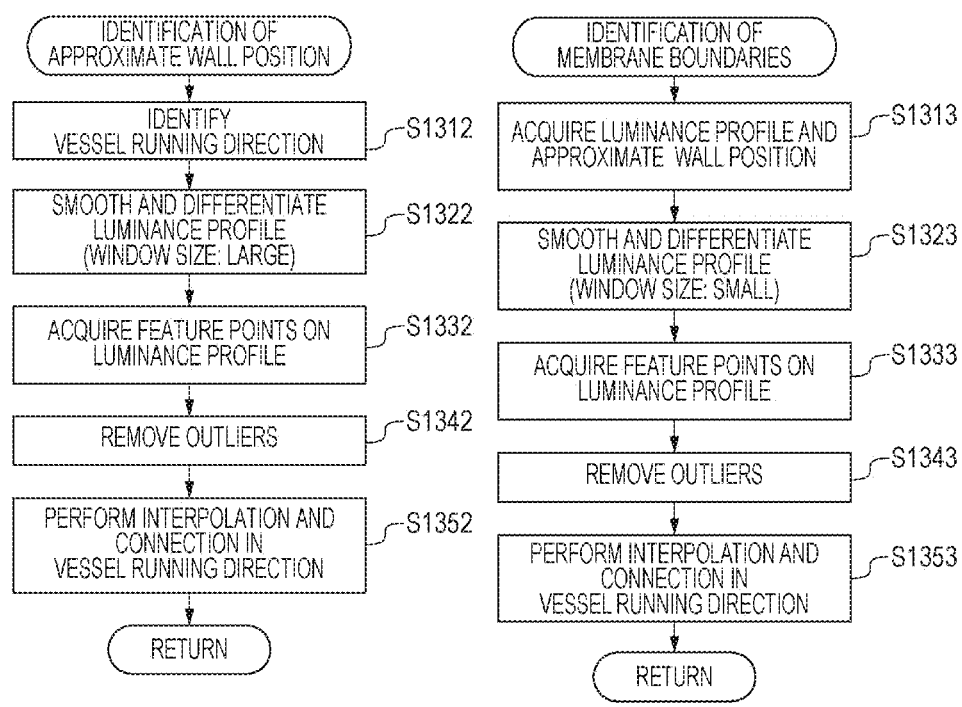

IMAGE PROCESSING APPARATUS AND IMAGE PROCESSING METHOD

BACKGROUND OF THE INVENTION

Field of the Invention

The present invention relates to an image processing apparatus and an image processing method used in ophthalmic practices.

Description of the Related Art

Subjects' eyes are often examined for the purpose of early diagnosis and treatment of lifestyle-related diseases and diseases that are leading causes of blindness. A scanning laser ophthalmoscope (SLO), which is an ophthalmic apparatus using the principles of confocal laser microscopes, is configured to raster-scan a laser beam (measuring beam) across a fundus and quickly acquire a high-resolution planar image from the intensity of light returned from the fundus.

By detecting only light that has passed through an opening (pinhole), only returned light at a particular depth can be converted into an image, which has a higher contrast than images that can be acquired by a fundus camera.

Hereinafter, an apparatus configured to capture such a planar image will be referred to as an SLO apparatus, and the planar image will be referred to as an SLO image.

By increasing the diameter of a measuring beam in the SLO apparatus, it has become possible in recent years to acquire an SLO image of a retina with higher lateral resolution. However, as the diameter of the measuring beam increases, degradation in signal-to-noise (S/N) ratio and resolution of the SLO image caused by aberration of the subject's eye has become a problem in acquiring an SLO image of the retina.

As a solution to this, an adaptive optics SLO apparatus including an adaptive optics system has been developed. The adaptive optics system is configured to measure the aberration of the subject's eye with a wavefront sensor in real time, and correct, with a wavefront correction device, the aberration of the measuring beam or returned light occurring in the subject's eye. With this adaptive optics SLO apparatus, an SLO image with high lateral resolution can be acquired.

This SLO image with high lateral resolution can be acquired as a moving image. For example, to noninvasively observe the circulation of blood, retinal vessels are extracted from each frame, and the transfer rate of blood cells in capillaries is measured. Also, to evaluate a relation with a visual function using the SLO image, visual cells P are detected, and the density distribution and arrangement of the visual cells P are measured. FIG. 6B illustrates an SLO image with high lateral resolution. This SLO image allows observation of a low-luminance region Q corresponding to the position of the visual cells P and capillaries, and a high-luminance region W corresponding to the position of a white blood cell.

For observation of the visual cells P, an SLO image, such as that illustrated in FIG. 6B, is captured with the focus position set near the outer layer of the retina (B4 in FIG. 6A). Retinal vessels and branched capillaries run through the inner layers of the retina (B1 to B3 in FIG. 6A). When an adaptive optics SLO image is acquired with the focus position set in an inner layer of the retina, it is possible to directly observe retinal vascular walls.

However, in a confocal image of the inner layer of the retina, strong noise signals caused by reflection of light from a nerve fiber layer may make it difficult to observe a vascular wall and detect wall boundaries.

Accordingly, a method of observing a non-confocal image has begun to be used in recent years. The non-confocal image is obtained by acquiring scattered light by varying the diameter, shape, and position of a pinhole in front of a light receiving portion. A large focus depth of the non-confocal image facilitates observation of an object having protrusions and recesses in the depth direction, such as a vessel. Also, since light reflected from the nerve fiber layer is not easily directly received, it is possible to achieve noise reduction.

A retinal artery is a small artery (arteriole) with a vessel diameter of about 10 μm to 100 μm. The wall of the retinal artery includes an intima, a media, and an adventitia. The media is formed by smooth-muscle cells, and runs in a coil-like manner in the circumferential direction of the vessel. For example, if hypertension causes increased pressure on the retinal arterial wall, the smooth muscle contracts and the wall thickness increases. At this point, the shape of the retinal arterial wall can be restored when the blood pressure is lowered, for example, by taking a blood pressure lowering drug. However, if the hypertension is left untreated for a long time, the smooth-muscle cells forming the media become necrotic, and fibrous thickening of the media and adventitia leads to an increase in wall thickness. At this point, organic (irreversible) damage already develops in the retinal arterial wall, and continuous treatment is required to prevent worsening of the arteriolar damage.

A technique for measuring retinal vessel diameters is disclosed in "Computer algorithms for the automated measurement of retinal arteriolar diameters" by Chapman et al., published in Br J Ophthalmol, Vol. 85, No. 1, pp. 74 to 79, 2001. In this technique, a luminance profile generated on a line segment substantially perpendicular to the running of a retinal vessel in an SLO image is linearly approximated for each small window. Then, positions corresponding to the maximum and minimum values of the slope of the resulting regression line are acquired as retinal vessel boundaries to measure the retinal vessel diameter. Additionally, a technique for semi-automatically extracting retinal vascular wall boundaries in an adaptive optics fundus camera image using a variable geometry model is disclosed in "Morphometric analysis of small arteries in the human retina using adaptive optics imaging: relationship with blood pressure and focal vascular changes" by Koch et al., published in Journal of Hypertension, Vol. 32, No. 4, pp. 890 to 898, 2014.

SUMMARY OF THE INVENTION

An image processing apparatus according to an aspect of the present invention includes a processing unit configured to perform, on a luminance distribution acquired in at least one direction crossing a vessel region in a fundus image of a subject's eye, a first smoothing operation for each first size and a second smoothing operation for each second size smaller than the first size; a first identifying unit configured to identify a position of a vascular wall in the fundus image on the basis of the luminance distribution obtained by performing the first smoothing operation; and a second identifying unit configured to identify positions of inner and outer boundaries of the vascular wall in the fundus image on the basis of the luminance distribution obtained by performing the second smoothing operation.

An image processing method according to another aspect of the present invention includes a processing step of performing, on a luminance distribution acquired in at least one direction crossing a vessel region in a fundus image of a subject's eye, a first smoothing operation for each first size and a second smoothing operation for each second size smaller than the first size; a first identifying step of identifying a position of a vascular wall in the fundus image on the basis of the luminance distribution obtained by performing the first smoothing operation; and a second identifying step of identifying positions of inner and outer boundaries of the vascular wall in the fundus image on the basis of the luminance distribution obtained by performing the second smoothing operation.

Further features of the present invention will become apparent from the following description of exemplary embodiments with reference to the attached drawings.

BRIEF DESCRIPTION OF THE DRAWINGS

FIG. 7 illustrates image processing in embodiments of the present invention.

FIG. 12 is a block diagram illustrating a functional configuration of an image processing apparatus according to a third embodiment of the present invention.

FIGS. 13A to 13D are flowcharts illustrating details of operations executed in steps S531 and S541 according to the third embodiment of the present invention.

DESCRIPTION OF THE EMBODIMENTS

Figure 1:
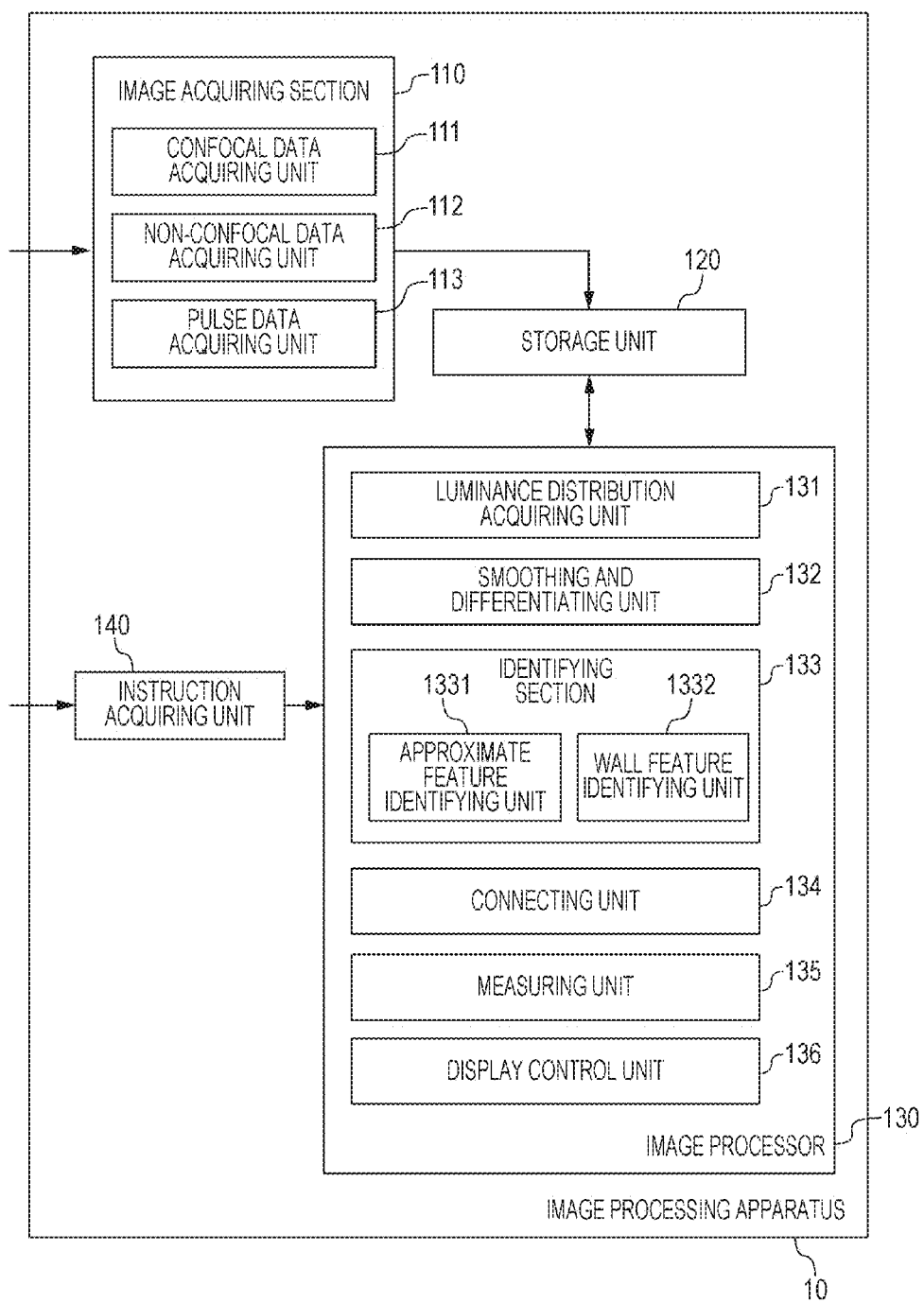
FIG. 1 is a block diagram illustrating a functional configuration of an image processing apparatus according to a first embodiment of the present invention.

Of all the arterioles in the body, the retinal arteries of the subject's eye are only tissues that are directly observable. For diagnosis of diabetes or hypertension, it is expected to accurately measure the thickness of the vascular walls of retinal arteries as a way of detecting the presence or degree of change in arterioles in the body. For the accurate measurement, it is required to easily and accurately identify the positions of the inner and outer boundaries of the vascular walls of retinal arteries.

An embodiment of the present invention provides a technique for easily and accurately identifying the positions of the inner and outer boundaries of a vascular wall in a fundus image of a subject's eye.

An image processing apparatus according to an embodiment includes a processing unit (e.g., smoothing and differentiating unit 132) configured to perform, on a luminance distribution acquired in at least one direction crossing a vessel region in a fundus image of a subject's eye, a first smoothing operation for each first size and a second smoothing operation for each second size smaller than the first size. The image processing apparatus according to the embodiment also includes a first identifying unit (e.g., approximate feature identifying unit 1331) configured to identify a position of a vascular wall in the fundus image on the basis of the luminance distribution obtained by performing the first smoothing operation. The image processing apparatus according to the embodiment also includes a second identifying unit (e.g., wall feature identifying unit 1332) configured to identify positions of inner and outer boundaries of the vascular wall in the fundus image on the basis of the luminance distribution obtained by performing the second smoothing operation. With this configuration, the positions of the inner and outer boundaries of the vascular wall in the fundus image of the subject's eye can be easily and accurately identified. The present invention may be configured in any manner as long as a smoothing operation is performed on a luminance distribution acquired in at least one direction. For example, the smoothing operation may be performed on the entire fundus image or the entire vessel region.

An image processing apparatus according to another embodiment includes a processing unit (e.g., smoothing and differentiating unit 132) configured to perform, on a luminance distribution acquired in at least one direction crossing a vessel region in a fundus image of a subject's eye, a smoothing operation with a first size and a second size smaller than the first size. The image processing apparatus according to the embodiment also includes a first identifying unit (e.g., approximate feature identifying unit 1331) configured to identify, as positions of a first vascular wall and a second vascular wall, a plurality of feature points in the luminance distribution obtained by performing the smoothing operation with the first size. The image processing apparatus according to the embodiment also includes a second identifying unit (e.g., wall feature identifying unit 1332) configured to identify, as positions of inner and outer boundaries of the first vascular wall and positions of inner and outer boundaries of the second vascular wall, a plurality of feature points near the identified positions of the first and second vascular walls in the luminance distribution obtained by performing the smoothing operation with the second size. With this configuration, the positions of the inner and outer boundaries of the vascular wall in the fundus image of the subject's eye can be easily and accurately identified. In related art, the operator manually measures the thicknesses of vascular walls and membranes of retinal arteries in the fundus image of the subject's eye (e.g., an image of the fundus of the subject's eye captured by an SLO apparatus to which an adaptive optics technique is applied). Therefore, the measurement is complex and less reproducible due to measurement errors caused by the operator. As a solution to this, in an image depicting vascular walls of the subject's eye and membranes and cells forming the vascular walls, wall boundaries and membrane boundaries may be automatically identified and the thicknesses of the vascular walls and membranes may be automatically measured. Accordingly, the image processing apparatus may further include a measuring unit configured to measure at least one of a vascular wall thickness, a vessel inner diameter, and a vessel outer diameter using the positions of the outer and inner boundaries of the first vascular wall and the positions of the outer and inner boundaries of the second vascular wall.

An image processing apparatus according to another embodiment includes a first identifying unit (e.g., approximate feature identifying unit 1331) configured to identify a position of a vascular wall in a fundus image of a subject's eye on the basis of a luminance distribution acquired in at least one direction crossing a vessel region in the fundus image. The image processing apparatus according to the embodiment also includes a second identifying unit (e.g., wall feature identifying unit 1332) configured to identify a plurality of feature points near the identified position of the vascular wall in the luminance distribution as positions of inner and outer boundaries of the vascular wall in the fundus image. With this configuration, the positions of the inner and outer boundaries of the vascular wall in the fundus image of the subject's eye can be easily and accurately identified. The document by Chapman et al. mentioned above discloses a technique of measuring a retinal vessel diameter by acquiring retinal vessel boundaries in an SLO image using a sliding linear regression filter. However, this document does not describe the technique of detecting the wall and membrane boundaries of a vessel in an adaptive optics SLO image depicting vascular walls and membranes, or the technique of automatically measuring the thicknesses of vascular walls and membranes. Also, the document by Koch et al. mentioned above discloses a technique of semi-automatically measuring the thickness of a retinal arterial wall by detecting retinal vascular wall boundaries in an adaptive optics fundus camera image using a variable geometry model. However, since the adaptive optics fundus camera image cannot depict vein walls and membranes forming the artery and vein walls, the document by Koch et al. does not describe the technique of detecting vein walls and membrane boundaries of arteries and veins, or the technique of measuring the thicknesses of vein walls and the thicknesses of vessel membranes of arteries and veins.

Embodiments of an image processing apparatus and an image processing method according to the present invention will now be described in detail with reference to the attached drawings. Note that the present invention is not limited to the embodiments described below.

First Embodiment

An image processing apparatus according to the present embodiment identifies wall boundaries in one of images obtained by smoothing a retinal vascular wall image at different scales (sizes) and differentiating the resulting images, the retinal vascular wall image being captured using an SLO apparatus configured to acquire confocal and non-confocal images, on the basis of feature points on a luminance profile (luminance distribution) acquired in a direction crossing the retinal vessel.

Specifically, a non-confocal image of retinal vascular walls captured using the SLO apparatus configured to simultaneously acquire confocal and non-confocal images is smoothed at two different scales (sizes) and differentiated. In the image smoothed at a large scale (first size) and differentiated, the approximate positions (representative positions) of the walls (first and second vascular walls) are identified on the basis of feature points on a luminance profile crossing the retinal vessel. In the image smoothed at a small scale (second size) and differentiated, wall boundary candidate points are acquired from feature points on a luminance profile crossing the retinal vessel, and connected in the vessel running direction after removal of outliers, so as to identify vascular wall boundaries and measure the wall thicknesses. In the present specification, the term "smoothing and differentiating operation" includes the concept of "differentiation (which may be either subtraction or division) performed on a luminance distribution obtained by smoothing", and also includes the concept of "linear approximation performed on a luminance distribution". Differentiation is not an essential operation for the present invention, but will be described in detail later on.

(General Configuration)

Figure 2:
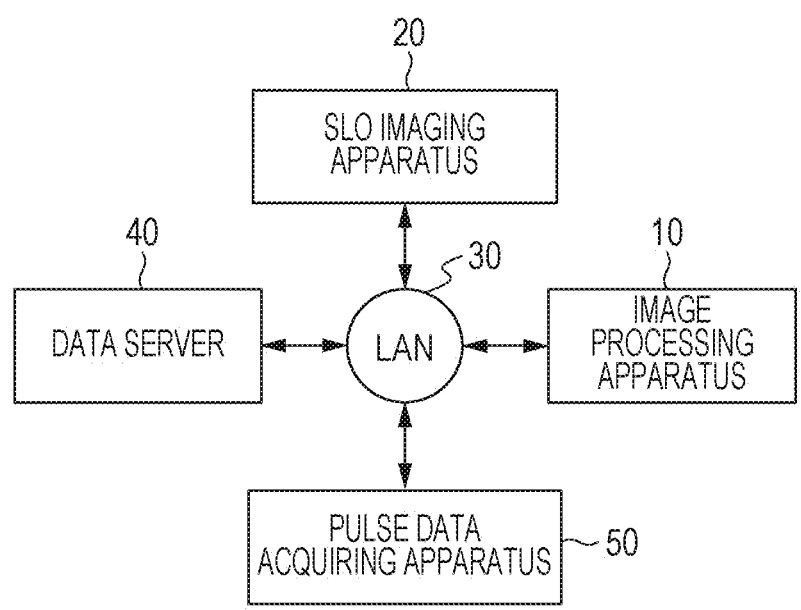
FIG. 2 is a block diagram illustrating a configuration of a system including the image processing apparatus according to an embodiment of the present invention.

FIG. 2 illustrates a configuration of a system including an image processing apparatus 10 according to the present embodiment. As illustrated in FIG. 2, the image processing apparatus 10 is connected to an SLO imaging apparatus 20, a data server 40, and a pulse data acquiring apparatus 50 through a local area network (LAN) 30 formed by an optical fiber, universal serial bus (USB), or IEEE 1394. The image processing apparatus 10 may be connected to these apparatuses either directly or through an external network, such as the Internet.

The SLO imaging apparatus 20 is an apparatus configured to capture a wide-field image Dl of the subject's eye, and a confocal image Dc and a non-confocal image Dn, which are high-magnification images, of the subject's eye. The SLO imaging apparatus 20 transmits, to the image processing apparatus 10 and the data server 40, the wide-field image Dl, the confocal image Dc, the non-confocal image Dn, and information of fixation target positions Fl and Fcn used to capture the images.

The pulse data acquiring apparatus 50 is an apparatus configured to acquire biological signal data (pulse data) that autonomously changes. For example, the pulse data acquiring apparatus 50 is formed by a sphygmograph or electrocardiograph. In response to an operation by an operator (not shown), the pulse data acquiring apparatus 50 acquires pulse data Pi simultaneously with the acquisition of the wide-field image Dl, the confocal image Dc, and the non-confocal image Dn. The acquired pulse data Pi is transmitted to the image processing apparatus 10 and the data server 40. The pulse data acquiring apparatus 50 may be configured to be directly connected to the SLO imaging apparatus 20.

When the images are acquired at different capturing positions, the acquired images are represented by Dli, Dcj, and Dnk, where i, j, and k are variables each representing a capturing position number as follows: i=1, 2, . . . , imax; j=1, 2, . . . , jmax; and k=1, 2, . . . , kmax. When the confocal image Dc and the non-confocal image Dn are each acquired at different magnifications, the acquired images are represented by Dc1*m*, Dc2*o*, . . . (Dn1*m*, Dn2*o*, . . . ) in the descending order of magnification. Note that Dc1*m* (Dn1*m*) will be referred to as a high-magnification confocal (non-confocal) image, and Dc2*o*, . . . (Dn2*o*, . . . ) will be referred to as a medium-magnification confocal (non-confocal) image.

The data server 40 is configured to hold the wide-field image Dl, the confocal image Dc, and the non-confocal image Dn of the subject's eye; condition data, such as the fixation target positions Fl and Fcn used to capture the images; the pulse data Pi; and image features of the subject's eye. As the image features of the subject's eye, the present invention deals with those related to retinal vessels, retinal vascular walls, and membranes and wall cells forming the vascular walls. The wide-field image Dl, the confocal image Dc, and the non-confocal image Dn output from the SLO imaging apparatus 20, the fixation target positions Fl and Fcn used to capture the images, the pulse data Pi, and the image features of the subject's eye output from the image processing apparatus 10 are stored in the data server 40. In response to a request from the image processing apparatus 10, the data server 40 transmits the wide-field image Dl, the confocal image Dc, the non-confocal image Dn, the pulse data Pi, and the image features of the subject's eye to the image processing apparatus 10.

A functional configuration of the image processing apparatus 10 according to the present embodiment will now be described with reference to FIG. 1. FIG. 1 is a block diagram illustrating a functional configuration of the image processing apparatus 10. The image processing apparatus 10 includes an image acquiring section 110, a storage unit 120, an image processor 130, and an instruction acquiring unit 140.

The image acquiring section 110 includes a confocal data acquiring unit 111, a non-confocal data acquiring unit 112, and a pulse data acquiring unit 113. The image processor 130 includes a luminance distribution acquiring unit 131, a smoothing and differentiating unit 132, an identifying section 133, a connecting unit 134, a measuring unit 135, and a display control unit 136. The identifying section 133 includes an approximate feature identifying unit 1331, which is an example of a first identifying unit, and a wall feature identifying unit 1332, which is an example of a second identifying unit.

The SLO imaging apparatus 20 to which adaptive optics is applied will be described with reference to FIGS. 3A and 3B. The SLO imaging apparatus 20 includes a super-luminescent diode (SLD) 201, a Shack-Hartmann wavefront sensor 206, an adaptive optics system 204, first and second beam splitters 202 and 203, an X-Y scanning mirror 205, a focus lens 209, an aperture 210, an optical sensor 211, an image forming unit 212, and an output unit 213.

Light emitted from the SLD 201 serving as a light source is reflected by the fundus. Part of the light is input to the Shack-Hartmann wavefront sensor 206 through the second beam splitter 203, and the remaining part of the light is input to the optical sensor 211 through the first beam splitter 202. The Shack-Hartmann wavefront sensor 206 is a device for measuring aberration of the eye. The Shack-Hartmann wavefront sensor 206 includes a lens array 207 and a charge-coupled device (CCD) 208 connected to the lens array 207. When incident light passes through the lens array 207, a group of luminous points appears on the CCD 208, and wavefront aberration is measured on the basis of positional deviation of the luminous points projected on the CCD 208. On the basis of the wavefront aberration measured by the Shack-Hartmann wavefront sensor 206, the adaptive optics system 204 drives an aberration correcting device (e.g., variable shape mirror or spatial optical phase modulator) to correct the aberration. The aberration-corrected light passes through the focus lens 209 and the aperture 210, and is received by the optical sensor 211. A scanning position on the fundus can be controlled by moving the X-Y scanning mirror 205. The optical sensor 211 acquires data of an image target region and time (i.e., frame rate×number of frames) specified in advance by the operator. The optical sensor 211 transmits the data to the image forming unit 212, which corrects image distortion caused by variation in scanning speed and also corrects luminance values to form image data (moving image or still image). The output unit 213 outputs the image data formed by the image forming unit 212.

Figure 3A:
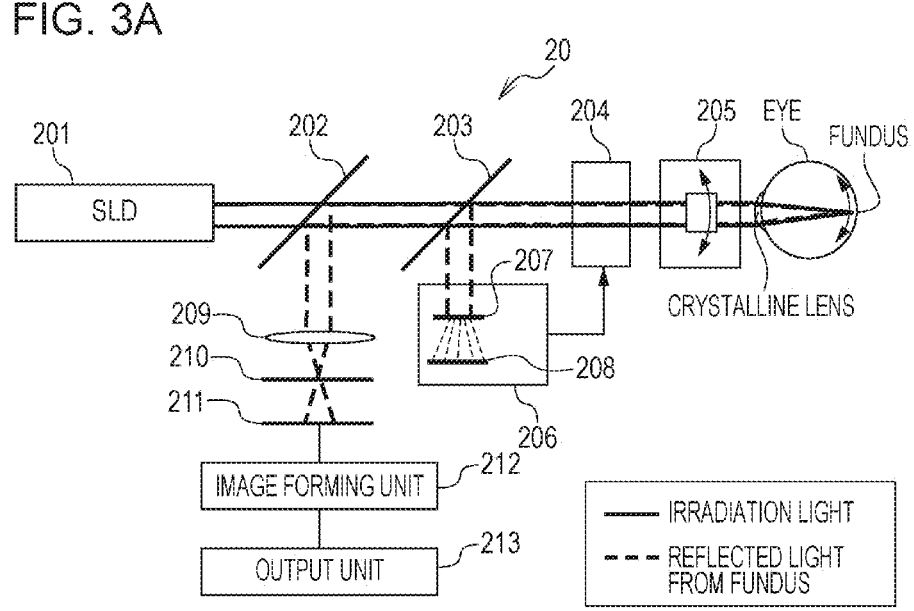
FIGS. 3A to 3H illustrate an overall configuration of an SLO imaging apparatus according to an embodiment of the present invention.
Figure 3B:
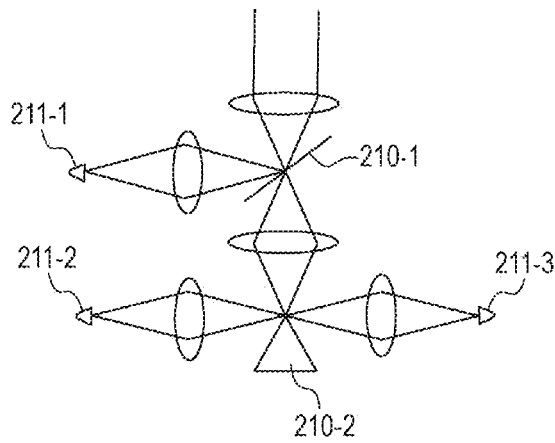

In the SLO imaging apparatus 20, the aperture 210 and the optical sensor 211 in FIG. 3A may have any configuration as long as the confocal image Dc and the non-confocal image Dn can be acquired. In the present embodiment, the aperture 210 is formed by a light-shielding portion 210-1 (see FIGS. 3B and 3E), and the optical sensor 211 is formed by optical sensors 211-1, 211-2, and 211-3 (see FIG. 3B). Referring to FIG. 3B, part of return light (reflected light or scattered light) incident on the light-shielding portion 210-1 disposed in the image forming plane is reflected and enters the optical sensor 211-1. The light-shielding portion 210-1 will now be described with reference to FIG. 3E. The light-shielding portion 210-1 is formed by transmission regions 210-1-2 and 210-1-3, a light-shielding region (not shown), and a reflection region 210-1-1. The light-shielding portion 210-1 is disposed such that its center is located in the center of the optical axis of the return light. When the light-shielding portion 210-1 is positioned at an angle with respect to the optical axis of the return light, the light-shielding portion 210-1 has an elliptical pattern, which is circular as viewed in the direction of the optical axis. Light split by the light-shielding portion 210-1 enters the optical sensor 211-1. Light passing through the transmission regions 210-1-2 and 210-1-3 of the light-shielding portion 210-1 is split by a prism 210-2 disposed in the image forming plane, and enters the optical sensors 211-2 and 211-3 as illustrated in FIG. 3B.

A voltage signal obtained by each optical sensor is converted to a digital value by an analog-to-digital (AD) board in the image forming unit 212, and then converted to a two-dimensional image. An image generated on the basis of the light incident on the optical sensor 211-1 is a confocal image that focuses on a specific narrow range. An image generated on the basis of the light incident on each of the optical sensors 211-2 and 211-3 is a non-confocal image that focuses on a wide range.

Figure 3C:
Figure 3D:
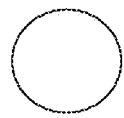
Figure 3E:
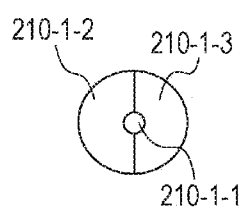
Figure 3F:
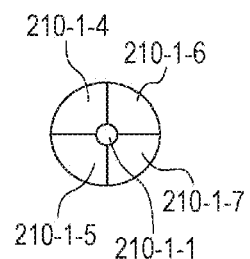
Figure 3G:
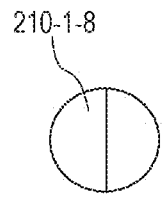
Figure 3H:
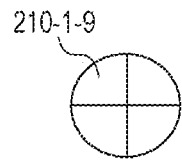

A non-confocal signal may be divided in other ways. For example, as illustrated in FIG. 3F, a non-confocal signal may be divided into four and received in transmission regions 210-1-4 to 210-1-7. Also, a confocal signal and a non-confocal signal may be received in other ways. For example, the diameter and position of the aperture 210 (opening) may be made variable, so that the aperture 210 can be adjusted to receive either a confocal signal as illustrated in FIG. 3C or a non-confocal signal as illustrated in FIG. 3D. The diameter and the amount of movement of the opening may be set to any values. For example, the diameter of the opening can be set to about 1 airy disc diameter (ADD) in FIG. 3C, whereas the diameter of the opening can be set to about 10 ADD and the amount of movement of the opening can be set to about 6 ADD in FIG. 3D. Alternatively, as illustrated in FIGS. 3G and 3H, a plurality of non-confocal signals may be received at substantially the same time in a transmission region 210-1-8 or 210-1-9.

Since there are two types of non-confocal signals in the present embodiment, a non-confocal image on one side (R channel image) is represented by Dnr and a non-confocal image on the other side (L channel image) is represented by Dnl.

The non-confocal image Dn refers to both the R channel image Dnr and the L channel image Dnl.

In the configuration of FIG. 3A, if the swing angle of a scanning optical system is increased and the adaptive optics system 204 is instructed not to perform aberration correction, the SLO imaging apparatus 20 can also operate as a normal SLO apparatus and can acquire a wide-field image.

Hereinafter, an image with a magnification lower than the high-magnification images Dc and Dn and lowest among images acquired by the image acquiring section 110 will be referred to as a wide-field image Dl (Dlc, Dln). This means that the wide-field image Dl may be an SLO image to which adaptive optics is applied, or may be a simple SLO image.

Figure 4:
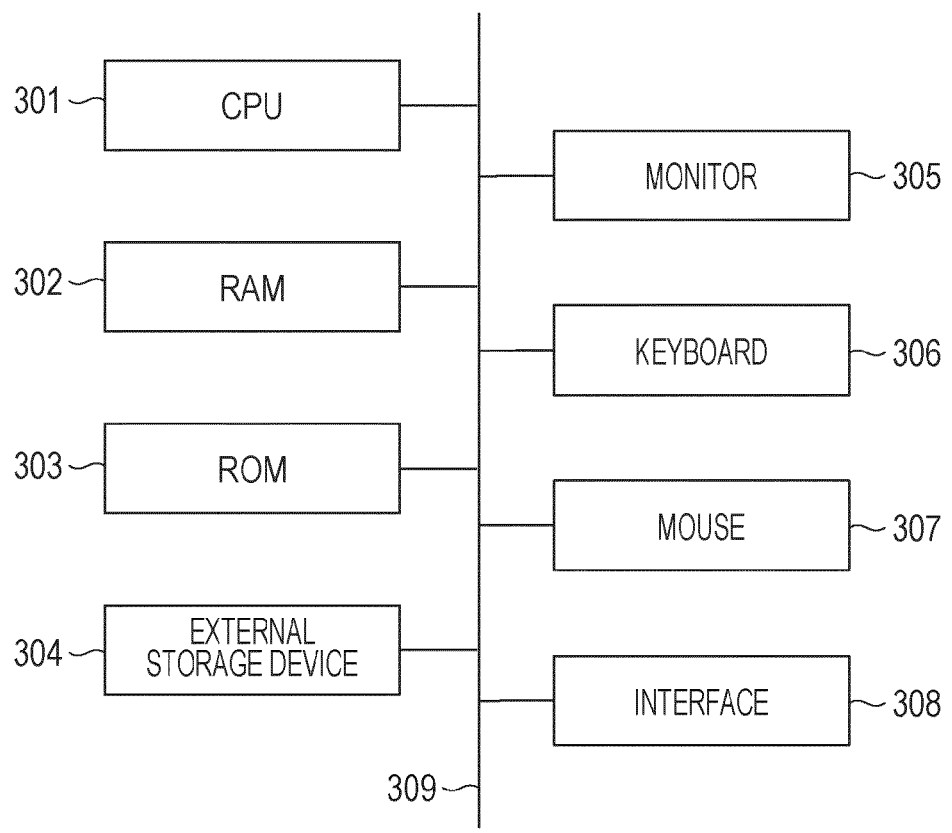
FIG. 4 is a block diagram illustrating a hardware configuration of a computer that includes hardware components corresponding to a storage unit and an image processor, holds other units as software components, and executes the software.

A hardware configuration of the image processing apparatus 10 will now be described with reference to FIG. 4. As illustrated in FIG. 4, the image processing apparatus 10 includes a central processing unit (CPU) 301, a memory (RAM) 302, a control memory (ROM) 303, an external storage device 304, a monitor 305, a keyboard 306, a mouse 307, and an interface 308. Control programs for implementing the image processing function of the present embodiment and data used to execute the control programs are stored in the external storage device 304. Under the control of the CPU 301, the control programs and data are appropriately loaded into the RAM 302 through a bus 309 and executed by the CPU 301, and then serve as the following units.

The functions of blocks forming the image processing apparatus 10 will be described in relation to an execution procedure of the image processing apparatus 10 illustrated in the flowchart of FIG. 5A.

(Step S510)

The image acquiring section 110 makes a request to the SLO imaging apparatus 20 to acquire the wide-field image Dl and the high-magnification images (confocal image Dcj, and non-confocal images Dnrk and Dnlk). The image acquiring section 110 also makes a request to the SLO imaging apparatus 20 to acquire the fixation target positions Fl and Fcn corresponding to these images. In response to the acquisition request, the SLO imaging apparatus 20 acquires the wide-field image Dl, the confocal image Dcj, the non-confocal images Dnrk and Dnlk, the corresponding attribute data, and the fixation target positions Fl and Fcn and transmits them to the image acquiring section 110. The image acquiring section 110 receives the wide-field image Dl, the confocal image Dcj, the non-confocal images Dnrk and Dnlk, and the fixation target positions Fl and Fcn from the SLO imaging apparatus 20 through the LAN 30, and stores them in the storage unit 120.

The pulse data acquiring unit 113 makes a request to the pulse data acquiring apparatus 50 to acquire the pulse data Pi related to a biological signal. In the present embodiment, a sphygmograph serving as the pulse data acquiring apparatus 50 acquires pulse wave data as the pulse data Pi from an earlobe of the subject. Here, the pulse data Pi is expressed as a sequence of points having the time of acquisition on one axis and a pulse wave signal value measured by the sphygmograph on the other axis. The pulse data acquiring apparatus 50 acquires and transmits the corresponding pulse data Pi in response to the acquisition request. The pulse data acquiring unit 113 receives the pulse data Pi from the pulse data acquiring apparatus 50 through the LAN 30. The pulse data acquiring unit 113 stores the received pulse data Pi in the storage unit 120.

The confocal data acquiring unit 111 or the non-confocal data acquiring unit 112 may start image acquisition in accordance with a specific phase of the pulse data Pi acquired by the pulse data acquiring apparatus 50, or the acquisition of the pulse data Pi and the image acquisition may be simultaneously started immediately after the request for image acquisition. In the present embodiment, the acquisition of the pulse data Pi and the image acquisition are simultaneously started immediately after the request for image acquisition.

The pulse data Pi for each image is acquired from the pulse data acquiring unit 113, and extremal values of each pulse data Pi are detected to calculate the cardiac beat cycle and the relative cardiac cycle. The relative cardiac cycle is a relative value expressed as a floating-point value ranging from 0 to 1, with the cardiac beat cycle being 1.

Figure 6A:
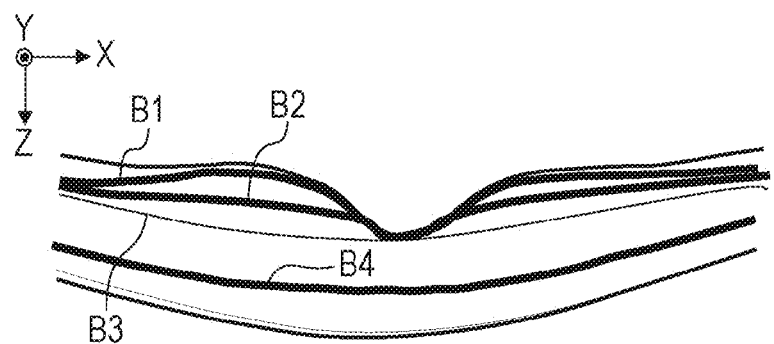
FIGS. 6A to 6M illustrate image processing in embodiments of the present invention.
Figure 6B:
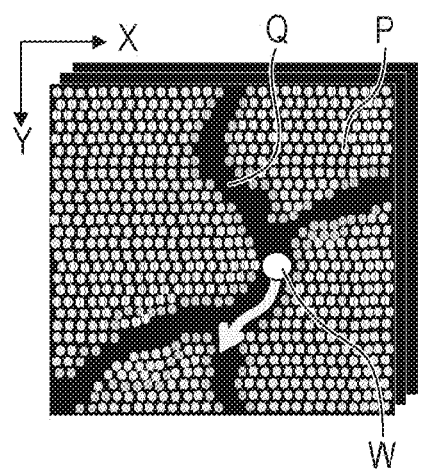
Figure 6C:
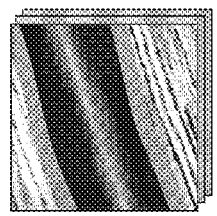
Figure 6D:
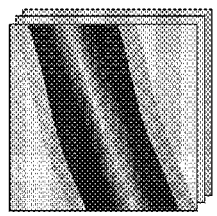
Figure 6E:
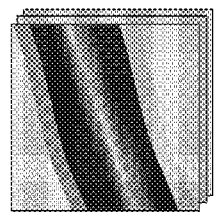

Examples of the confocal image Dc and the non-confocal image Dnr of a retinal vessel are illustrated in FIGS. 6C and 6D. In the confocal image Dc, reflection from a nerve fiber layer on the background is strong, and this often makes registration difficult due to the background noise. In the non-confocal image Dnr on the R channel, the contrast of the vascular wall on the right side is higher. In the non-confocal image Dnl on the L channel (see FIG. 6E), the contrast of the vascular wall on the left side is higher.

Figure 6F:
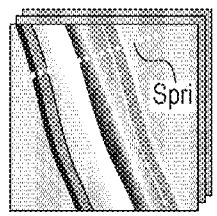
Figure 6G:
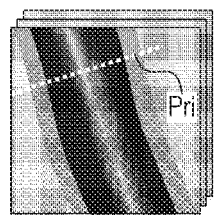
Figure 6H:
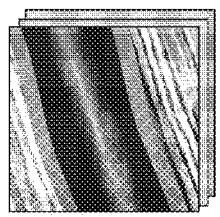

One of the following images (a) and (b), each obtained by arithmetic operation between the R channel image and the L channel image, may be used as a non-confocal image to observe and measure the vascular walls:

(a) averaged image Dnr+l of the R channel image and the L channel image (see FIG. 6G); and (b) split detector image Dns obtained by a difference enhancing operation between non-confocal images ((L−R)/(R+L)) (see FIG. 6F).

High-magnification images acquired at any position may be used. For example, the present invention includes the case of using images acquired around the optic disk, or images acquired along the retinal vessel arcade.

(Step S520)

The image processor 130 performs inter-frame registration of the acquired images. Next, the image processor 130 determines exception frames on the basis of the luminance value and noise of each frame and the amount of displacement from a reference frame.

The image processor 130 first performs inter-frame registration in the wide-field image Dl and the confocal image Dc, and applies parameter values for the inter-frame registration to each of the non-confocal images Dnr and Dnl.

Examples of the technique for the inter-frame registration include the following.

(i) The image processor 130 sets a reference frame serving as a reference for the registration. In the present embodiment, a frame with the smallest frame number is defined as a reference frame. The method for setting a reference frame is not limited to this, and any method may be used.

(ii) The image processor 130 establishes rough positional correspondences (i.e., performs rough registration) between frames. Although any registration technique can be used, the present embodiment performs rough registration using a correlation coefficient as an inter-image similarity evaluation function and also using affine transformation as a coordinate transformation technique.

(iii) The image processor 130 performs precise registration on the basis of data on rough positional correspondences between frames.

The present embodiment performs precise registration between frames of a moving image obtained after the rough registration in (ii) using a free-form deformation (FFD) technique, which is a kind of non-rigid registration techniques.

The technique for precise registration is not limited to this, and any registration technique may be used.

In the present embodiment, registration parameters obtained by performing inter-frame registration of the confocal image Dc are used as inter-frame registration parameters for the non-confocal image Dn, but the present invention is not limited to this. For example, the present invention also includes the case of using registration parameters obtained by inter-frame registration of the non-confocal image Dn (including Dnr, Dnl, and an image obtained by arithmetic operation between Dnr and Dnl) as inter-frame registration parameters for the confocal image Dc.

Next, the image processor 130 performs registration between the wide-field image Dl and the high-magnification image Dcj, and determines the relative position of the high-magnification image Dcj on the wide-field image Dl.

From the storage unit 120, the image processor 130 acquires the fixation target position Fcn used to capture the high-magnification image Dcj, and uses the fixation target position Fcn as an initial search point for the registration parameters for registration between the wide-field image Dl and the high-magnification image Dcj. The image processor 130 performs registration between the wide-field image Dl and the high-magnification image Dcj while varying the combination of the parameter values.

A combination of registration parameter values having the highest similarity between the wide-field image Dl and the high-magnification image Dcj is determined as the relative position of the high-magnification image Dcj with respect to the wide-field image Dl. The registration technique is not limited to this, and any registration technique may be used.

If a medium-magnification image has been acquired in step S510, registration of images is performed in the ascending order of magnification. For example, if the high-magnification confocal image Dc1$m$ and the medium-magnification confocal image Dc2$o$ have been acquired, registration between the wide-field image Dl and the medium-magnification confocal image Dc2$o$ is performed first, and then registration between the medium-magnification confocal image Dc2$o$ and the high-magnification confocal image Dc1$m$ is performed.

Additionally, image-combining parameter values determined for the wide-field image Dl and the confocal image Dcj are also applied to combining the non-confocal images Dnrk and Dnlk. The relative position of each of the non-confocal images Dnrk and Dnlk on the wide-field image Dl is determined.

(Step S530)

The approximate feature identifying unit 1331, which is an example of the first identifying unit, identifies the approximate position of each vascular wall in the following procedure.

(i) After frame averaging of the non-confocal moving images obtained after the inter-frame registration in step S520, the resulting image is smoothed at two different scales (sizes). The smoothed images are differentiated to generate smoothed and differentiated images. The smoothing is performed on the entire image in the present embodiment, but may be performed on a luminance distribution in at least one direction crossing a vessel region in a fundus image. In the fundus image, differentiation may be performed in two directions perpendicular to each other. However, when a luminance distribution in a direction crossing a vessel region is differentiated, the differentiation may be performed along the direction crossing the vessel region.

(ii) Of the smoothed and differentiated images generated in (i), the image obtained by differentiating the image smoothed at a small scale is subjected to a morphological filter to detect the center line of the retinal vessel.

(iii) Of the smoothed and differentiated images generated in (i), the image obtained by performing a first smoothing operation at a large scale (i.e., with a large filter size or large filter coefficient), which is defined as a first size, is subjected to a first differentiating operation. At each position on the vessel center line in the smoothed and differentiated image obtained by performing the first differentiating operation, a luminance profile (luminance distribution) is acquired on a line segment substantially perpendicular to the vessel center line.

(iv) On the luminance profile generated in (iii), the maximum and minimum values are detected in the rightward and leftward directions, respectively, to identify the approximate positions of walls. After grouping approximate position candidate points for each of the left wall and the right wall, which are a first vascular wall and a second vascular wall, respectively, the distances from the approximate position candidate points of each wall to the vessel center line are calculated. A predetermined percentage of the distance values at the top and bottom in each group are considered as outliers, and the approximate position candidate points having the outliers are removed. Then, the remaining approximate position candidate points of each wall are interpolated in the wall running direction. The technique for determining the outliers is not limited to that based on the distance values from the center line as in the present embodiment, and any known technique may be used to determine the outliers.

The process of identifying the approximate wall positions will be described in detail later on in steps S810 to S860.

(Step S540)

The wall feature identifying unit 1332, which is an example of the second identifying unit, identifies vascular wall boundary positions in the following procedure.

(i) Of the smoothed and differentiated images generated in (i) of step S530, the image obtained by performing a second smoothing operation at the small scale (i.e., with a small filter size or small filter coefficient), which is defined as a second size, is subjected to a second differentiating operation. At each position on the vessel center line in the smoothed and differentiated image obtained by performing the second differentiating operation, a luminance profile (luminance distribution) is acquired on a line segment substantially perpendicular to the vessel center line. Also, the approximate wall positions identified in (iv) of step S530 are acquired.

(ii) On the luminance profile acquired in (i), two local maximum points near the approximate wall position on the right side and two local minimum points near the approximate wall position on the left side are detected, and the detected points are defined as wall boundary candidate points. The wall boundary candidate points are grouped into four groups: an outer boundary of the left wall, an inner boundary of the left wall, an outer boundary of the right wall, and an inner boundary of the right wall. Then, the first-order moment (i.e., "distance from the center line"× "luminance value") is calculated for each wall boundary candidate point. Here, a luminance value in the non-confocal image (R+L image) is referenced as the luminance value. The technique for determining outliers is not limited to that based on the first-order moment as in the present embodiment, and any known technique may be used to determine the outliers. In each group, a predetermined percentage of the moment values at the top and bottom are considered as outliers, and the wall boundary candidate points having the outliers are removed. Then, the remaining wall boundary candidate points are interpolated in the wall running direction to identify the wall boundary.

The process of identifying the wall boundaries will be described in detail later on in steps S811 to S841.

(Step S550)

On the basis of the positions of the vascular wall boundaries identified in step S540, the measuring unit 135 measures the distribution of wall thickness along the running of the vessel, and the distribution of index value related to the wall thickness.

Specifically, the measuring unit 135 calculates the wall thickness of the detected wall, the inner and outer diameters of the vessel, and the index value (wall-to-lumen ratio (WLR)=(vessel outer diameter−vessel inner diameter)/(vessel inner diameter)) related to the wall thickness, and then determines the average value, standard deviation, and maximum and minimum values. These statistical values may be calculated not only for the entire image, but also for each branch vessel. Also, the statistical values of the wall thickness and the index value related to the wall thickness may be calculated for each side (i.e., right or left side in the vessel running direction) within the branch vessel, or may be calculated for each small region.

The index value related to the vascular wall thickness is not limited to this, and may be calculated by arithmetic operation of wall thickness values calculated for walls on both the right and left sides. For example, the wall thickness ratio between the right and left sides, as viewed in the vessel running direction, may be calculated. Since wall cells forming the majority of the vascular wall run in a coil-like manner, abnormalities in wall thickness are likely to occur on both sides. Therefore, the wall thickness ratio is used as an index for reliability of the measured wall thickness values.

(Step S560)

Figure 9A:
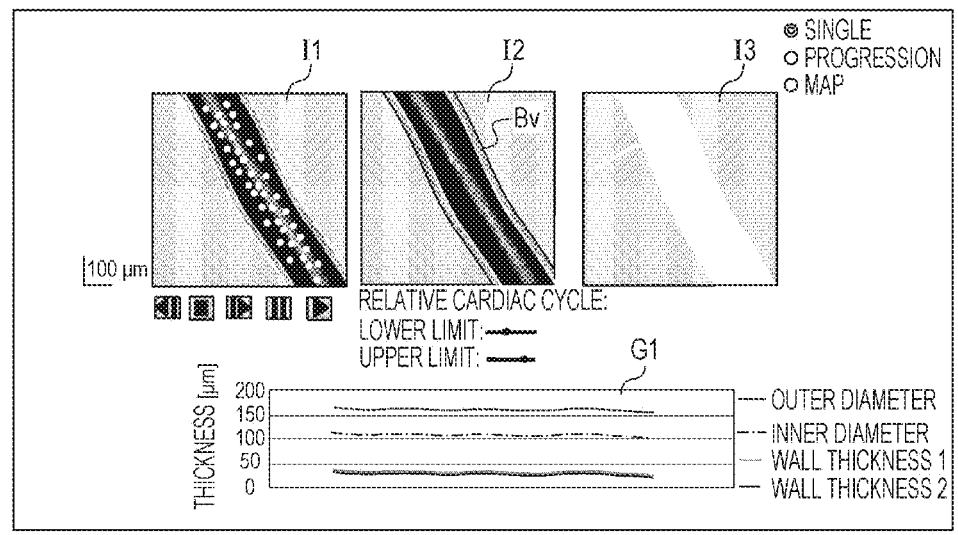
FIGS. 9A and 9B each illustrate data displayed in step S560 according to an embodiment of the present invention.
Figure 9B:
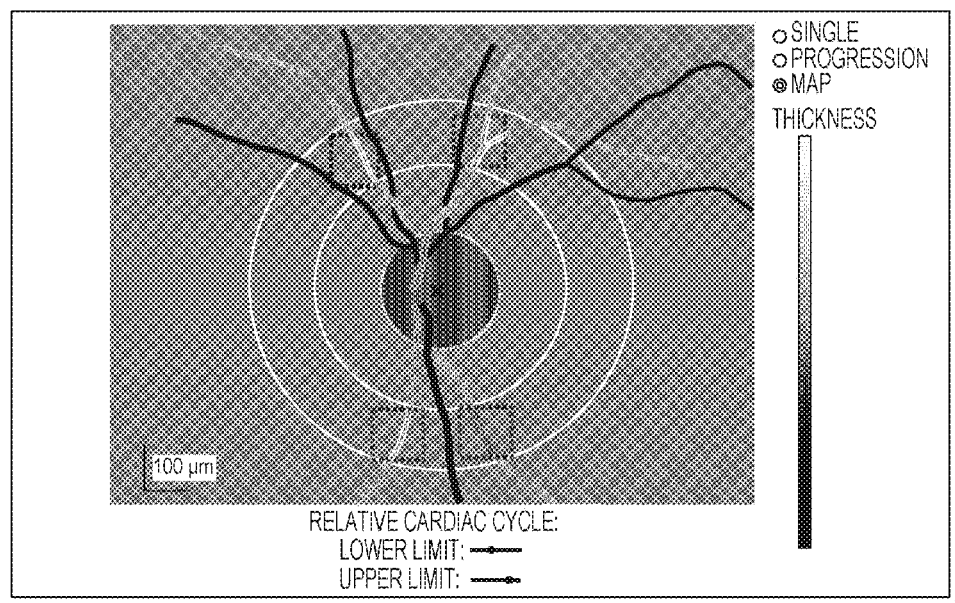

The display control unit 136 displays the acquired images, the positions of detected wall boundaries, and the measurement result (the wall thickness and the index value related thereto) on the monitor 305. In the present embodiment, the display control unit 136 displays the following (i) to (iv) on the monitor 305:

(i) non-confocal moving image (I1 in FIG. 9A),
  image obtained by selecting frames corresponding to a specific phase of a pulse wave and averaging the frames (I2 in FIG. 9A), and
  image extracting the lumen of the vessel for comparison (I3 in FIG. 9A);

(ii) detected wall boundary positions (Bv in FIG. 9A);

(iii) graph showing the wall thickness measured along the running of the vascular wall or the index value related to the wall thickness (G1 in FIG. 9A); and (iv) map showing the distribution of the wall thickness calculated for each small region or the index value related to the wall thickness (FIG. 9B).

For (iv), the display control unit 136 associates the calculated values with a color bar and displays them in color.

(Step S570)

The instruction acquiring unit 140 externally acquires an instruction as to whether to store the images acquired in step S510 and data measured in step S550 (i.e., wall boundary positions and wall thickness values in the non-confocal image Dnk) in the data server 40. For example, this instruction is input by the operator with the keyboard 306 or the mouse 307. If an instruction to store the images and data described above is acquired, the process proceeds to step S580, and if not, the process proceeds to step S590.

(Step S580)

The image processor 130 associates the examination date and information identifying the subject's eye with the images and the measurement-related data (determined to be stored in step S570), and transmits them to the data server 40.

(Step S590)

The instruction acquiring unit 140 externally acquires an instruction as to whether to end the process performed by the image processing apparatus 10 for the non-confocal image Dnk. This instruction is input by the operator with the keyboard 306 or the mouse 307. If an instruction to end the process is acquired, the process ends here. If an instruction to continue the process is acquired, the process returns to step S510, where the operation on the next subject's eye (or the same subject's eye) is performed.

Figure 8A:
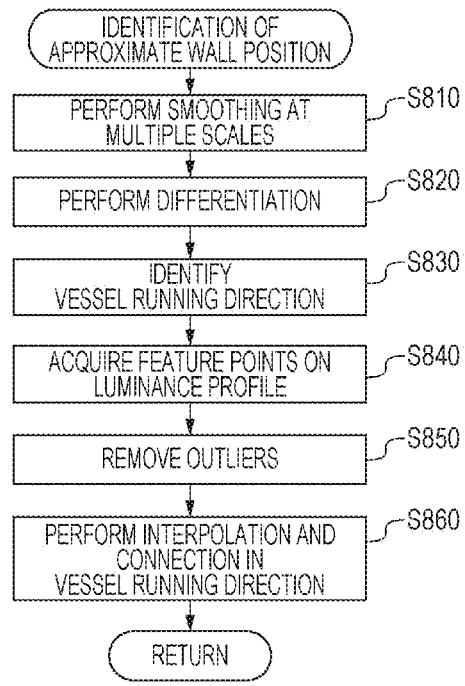
FIGS. 8A to 8D are flowcharts illustrating details of operations executed in steps S530 and S540 according to the first embodiment of the present invention.

Details of the operation performed in step S530 of FIG. 5A will be described with reference to FIGS. 6A to 6M, FIG. 7, and the flowchart of FIG. 8A.

(Step S810)

The smoothing and differentiating unit 132 performs smoothing, at multiple scales, on the non-confocal moving images obtained after the inter-frame registration. Any known smoothing operation is applicable here. In the present embodiment, after frame averaging of non-confocal moving images Dr+l obtained by inter-frame registration, the resulting image is subjected to a mean filter with filter sizes of 4 and 10.

(Step S820)

Figure 6I:
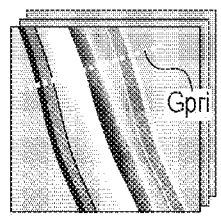
Figure 6J:
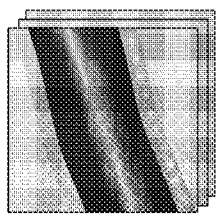

The smoothing and differentiating unit 132 performs differentiation on the smoothed images generated in step S810. Although any known differentiating operation is applicable, a differential edge detection operator is used in the present embodiment. As illustrated in FIG. 6I, the resulting smoothed and differentiated images are similar to an image obtained by smoothing the split detector image Dns (see FIG. 6F).

(Step S830)

The luminance distribution acquiring unit 131 applies a morphological filter to the image smoothed with a smaller filter size in step S810, so as to detect the center line of the retinal artery. In the present embodiment, the luminance distribution acquiring unit 131 uses a top-hat filter to detect a narrow-width, high-luminance region corresponding to reflection from the vascular wall. Then, the luminance distribution acquiring unit 131 performs thinning on the high-luminance region to detect the vessel center line. The method for detecting the vessel center line is not limited to this, and any known detecting method may be used.

(Step S840)

At each position on the vessel center line in the image (see FIG. 6I) differentiated after being smoothed at a large scale, the luminance distribution acquiring unit 131 generates a luminance profile Gpri1 (702 in FIG. 7, i=0, 1, 2, . . . , N) along a line segment perpendicular to the vessel center line.

Additionally, the approximate feature identifying unit 1331 searches luminance values on the luminance profile Gpri1 (702 in FIG. 7) to acquire a minimum value Gmin and a maximum value Gmax on the left and right sides, respectively, of a center line position G0, thereby identifying approximate wall position candidates.

(Step S850)

The image processor 130 groups the approximate wall position candidates identified on the luminance profiles in step S840 into the following two groups:

(i) approximate position candidate group for the left wall, and (ii) approximate position candidate group for the right wall.

Then, the image processor 130 determines outliers in each approximate position candidate group and removes them. In the present embodiment, a top Tt1% and a bottom Tb1% in terms of the distance from the vessel center line are considered as outliers, and approximate position candidates having the corresponding distance values are removed.

(Step S860)

The connecting unit 134 interpolates the remaining approximate wall position candidates in the vessel running direction and connects them to identify the vascular wall boundary. Any known technique may be used for the interpolation and connection. In the present embodiment, a natural spline interpolation method is used to interpolate and connect the approximate wall position candidates.

Figure 8B:
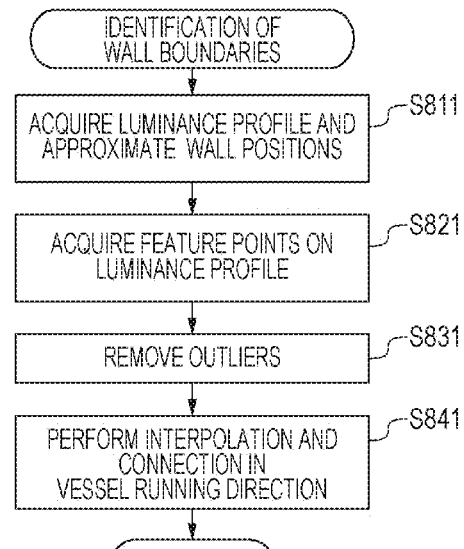

Details of the operation performed in step S540 of FIG. 5A will now be described with reference to FIGS. 6A to 6M, FIG. 7, and the flowchart of FIG. 8B.

(Step S811)

At each position on the vessel center line in the image differentiated after being smoothed at the small scale, a luminance profile Gpri2 (703 in FIG. 7, i=0, 1, 2, ..., N) along a line segment perpendicular to the vessel center line and approximate wall positions Gmin and Gmax are acquired.

(Step S821)

In the luminance profile Gpri2 acquired in step S811, the wall feature identifying unit 1332 selects two local minimum values near the approximate wall position Gmin and two local maximum values near the approximate wall position Gmax to identify wall boundary candidate positions.

(Step S831)

The image processor 130 groups the wall boundary candidates identified on the luminance profiles in step S821 into the following four groups:

(i) outer boundary candidate group for the left wall,
(ii) inner boundary candidate group for the left wall,
(iii) outer boundary candidate group for the right wall, and
(iv) inner boundary candidate group for the right wall.

Then, the image processor 130 determines outliers in each boundary candidate group and removes them. In the present embodiment, the first-order moment (i.e., "luminance value"ב"distance from the vessel center line") is calculated for each boundary candidate group. Then, a top Tt2% and a bottom Tb2% are considered as outliers, and wall boundary candidates having the corresponding moment values are removed. Here, a luminance value in the non-confocal image (R+L image) is referenced as the luminance value.

(Step S841)

The connecting unit 134 interpolates the remaining wall boundary candidate points for each boundary candidate group in the vessel running direction and connects them to identify the vascular wall boundary. Any known technique may be used for the interpolation and connection. In the present embodiment, a natural spline interpolation method is used to interpolate and connect the wall boundary candidate points.

Figure 8C:
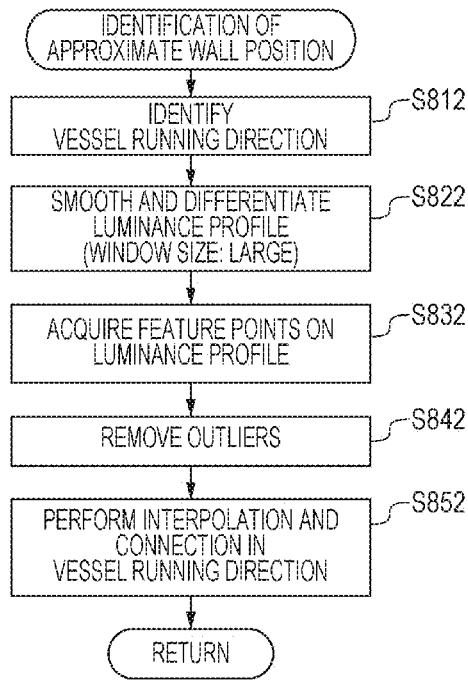
Figure 8D:
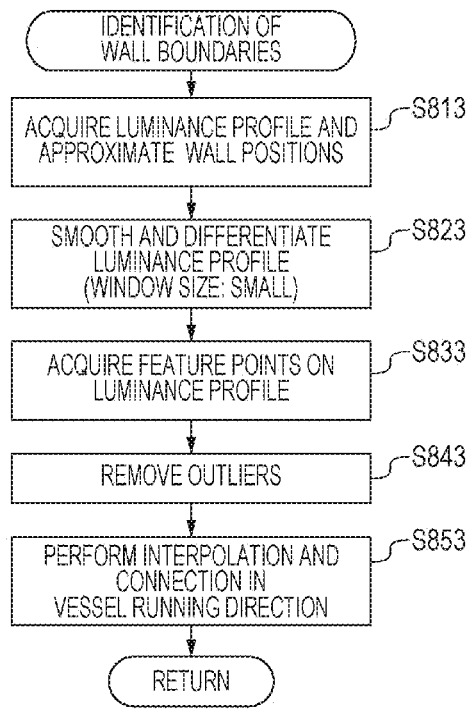

For smoothing and differentiating a luminance profile, the present embodiment applies a smoothing filter and a differentiating filter to a non-confocal image to acquire a luminance profile on the smoothed and differentiated image. However, the present invention is not limited to this. For example, in the procedures illustrated in FIGS. 8C and 8D, a luminance profile is acquired in a direction crossing a vessel in a non-confocal image. The present invention also includes the case of generating a smoothed and differentiated luminance profile by repeating the process which involves linearly approximating the luminance profile in each small window and outputting the slope of the regression line while moving the small window at regular intervals. In this case, only luminance values on the luminance profile, instead of the entire image, are smoothed and differentiated. A first linear approximation may be performed in a window of large size corresponding to the first scale, and a second linear approximation may be performed in a window of small size corresponding to the second scale.

Although the present embodiment identifies vascular wall boundaries in the non-confocal moving images Dr+l, the present invention is not limited to this. For example, the present invention also includes the case of identifying wall boundaries in the confocal image Dc by applying the image processing technique described in the present embodiment.

In the present embodiment, a single type of non-confocal image (R+L image) is smoothed at different scales and differentiated, so as to identify approximate vascular wall positions and vascular wall boundaries on the basis of feature points on a luminance profile in the smoothed and differentiated image. However, the present invention is not limited to this. For example, different types of non-confocal images (R channel image and L channel image) are differentiated after being smoothed at different scales. The approximate position and the wall boundaries of the vascular wall on the left side are identified by referring to a luminance profile in the image obtained by smoothing and differentiating the L channel image, and the approximate position and the wall boundaries of the vascular wall on the right side are identified by referring to a luminance profile in the image obtained by smoothing and differentiating the R channel image. This is also included in the present invention.

The present embodiment deals with the case in which, when a moving image obtained after registration is smoothed at different scales, the smoothing is performed with different filter sizes after frame averaging. However, the present invention is not limited to this. For example, the present invention also includes the case in which an image obtained by frame averaging alone is used as an image smoothed at a small scale, and an image obtained by in-plane smoothing after frame averaging is used as an image smoothed at a large scale. The present invention also includes the case in which two-dimensional images smoothed at different scales are generated by applying a three-dimensional smoothing filter having different filter sizes in the in-plane direction to a moving image obtained after inter-frame registration. In the case of performing frame averaging, frames corresponding to a specific phase of a pulse wave may be selected and averaged, so as to prevent the positions of membrane boundaries forming the vascular wall from being changed by the impact of cardiac beats.

Although the present embodiment deals with the case of automatically acquiring a vessel center line using a morphological filter, the present invention is not limited to this. For example, the present invention also includes the case of manually setting a vessel center line by acquiring, from the instruction acquiring unit 140, the position of the vessel center line specified by the operator using the keyboard 306 or the mouse 307.

With the configuration described above, in images obtained by smoothing a retinal vascular wall image at different scales and differentiating the resulting images, the retinal vascular wall image being captured using an SLO apparatus configured to acquire confocal and non-confocal images, the image processing apparatus 10 identifies wall boundaries on the basis of feature points on luminance profiles acquired in a direction crossing the vessel.

Thus, a vascular wall region can be easily and robustly identified in an image of the subject's eye.

Second Embodiment

An image processing apparatus according to the present embodiment performs the following processing on an image captured by an SLO apparatus configured to acquire a plurality of types of non-confocal images. First, the image processing apparatus smoothes two types of non-confocal images at different scales. Additionally, the image processing apparatus performs a subtraction operation between different types of non-confocal images smoothed at a large scale to generate a split detector image smoothed at a large scale. Also, the image processing apparatus performs a subtraction operation between different types of non-confocal images smoothed at a small scale to generate a split detector image smoothed at a small scale. A description will now be given of the case where, by using the same technique as the first embodiment, the approximate position of each vascular wall is identified in the split detector image smoothed at the large scale and vascular wall boundaries are identified in the split detector image smoothed at the small scale.

The configuration of devices connected to the image processing apparatus 10 according to the present embodiment will not be described here, as it is the same as that in the first embodiment.

Figure 10:
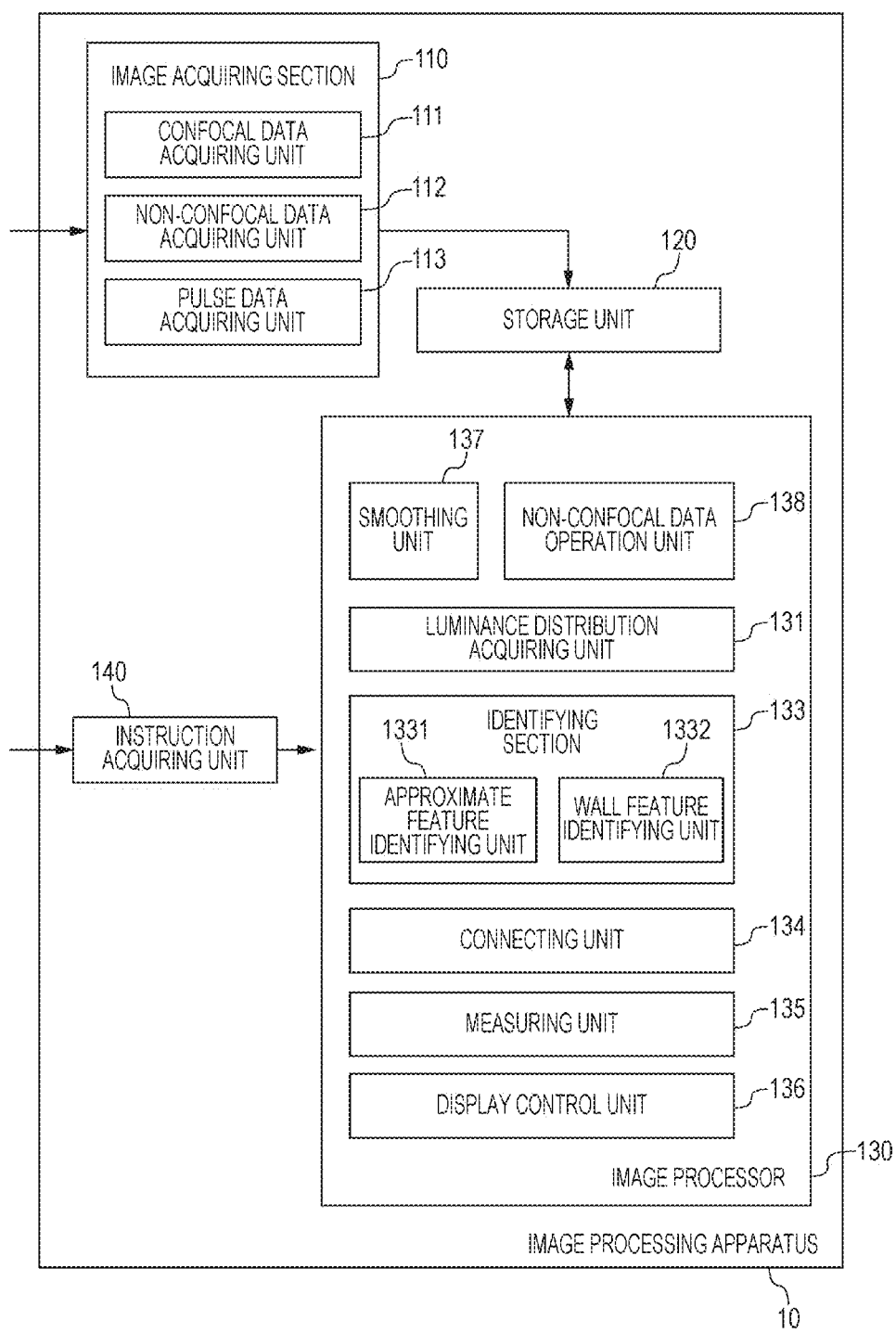
FIG. 10 is a block diagram illustrating a functional configuration of an image processing apparatus according to a second embodiment of the present invention.

FIG. 10 illustrates functional blocks of the image processing apparatus 10 according to the present embodiment. The present embodiment differs from the first embodiment in that the image processor 130 includes a smoothing unit 137 and a non-confocal data operation unit 138, instead of the smoothing and differentiating unit 132.

Figure 5A:
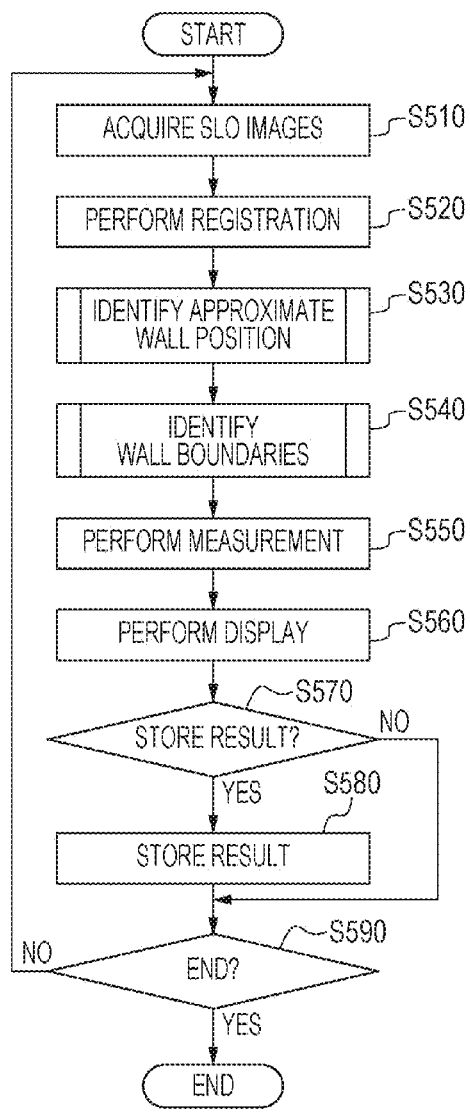
FIGS. 5A and 5B are each a flowchart illustrating a process executed by the image processing apparatus according to an embodiment of the present invention.

The image processing flow of the present embodiment is as illustrated in FIG. 5A, and steps other than steps S530 and S540 will not be described as they are the same as those in the first embodiment.
(Step S530)

The approximate feature identifying unit 1331 identifies the approximate position of each vascular wall in the following procedure.

(i) After frame averaging of the non-confocal moving images obtained after the inter-frame registration in step S520, the resulting image is smoothed at two different scales.

(ii) By performing a subtraction operation between different types of non-confocal images smoothed at a large scale and a subtraction operation between different types of non-confocal images smoothed at a small scale, two split detector images of different smoothing scales are generated.

(iii) Of the images smoothed in (i), the non-confocal image smoothed at the small scale is subjected to a morphological filter to detect the center line of the retinal vessel.

(iv) At each position on the vessel center line in one of the images generated in (ii), the one being a split detector image smoothed at the large scale, a luminance profile is acquired on a line segment substantially perpendicular to the vessel center line.

(v) On the luminance profile generated in (iv), the maximum and minimum values are detected in the rightward and leftward directions, respectively, to identify the approximate positions of walls. After grouping the approximate position candidate points for each of the left and right walls, the distances from the approximate position candidate points of each wall to the vessel center line are calculated. A predetermined percentage of the distance values at the top and bottom in each group are considered as outliers, and the approximate position candidate points having the outliers are removed. Then, the remaining approximate position candidate points of each wall are interpolated in the wall running direction. Any known technique may be used to determine the outliers.

Figure 11A:
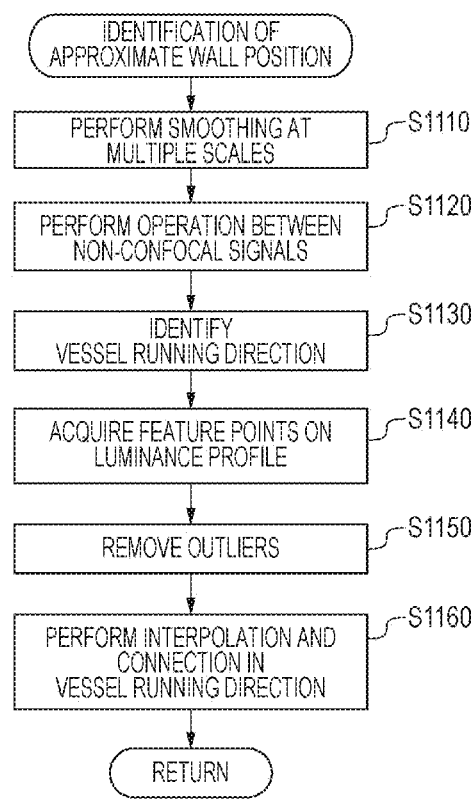
FIGS. 11A and 11B are flowcharts illustrating details of operations executed in steps S530 and S540 according to the second embodiment of the present invention.

Details of the operation performed in step S530 of FIG. 5A will be described with reference to FIG. 7 and the flowchart of FIG. 11A. Note that steps S1130, S1150, and S1160 will not be described here, as they are the same as the corresponding steps in the first embodiment.
(Step S1110)

The smoothing unit 137 performs smoothing, at multiple scales, on the non-confocal moving images obtained after the inter-frame registration. Any known smoothing operation is applicable here. In the present embodiment, after frame averaging of non-confocal moving images Dnr and Dnl obtained by inter-frame registration, the resulting image is subjected to a Gaussian filter with filter sizes of 4 and 10.
(Step S1120)

The non-confocal data operation unit 138 performs a subtraction operation between different types of non-confocal images smoothed in step S1110. In the present embodiment, a difference enhancing operation is performed using the R channel image and the L channel image smoothed at the same scale ($(L-R)/(R+L)$) to generate a smoothed split detector image (see FIG. 6F). The operation performed here is not limited to this, and any known operation having the same effect as differentiation may be applied. Instead of performing the subtraction operation described above, the non-confocal data operation unit 138 may perform a division operation between different types of smoothed non-confocal images.
(Step S1140)

At each position on the vessel center line in the split detector image (see FIG. 6F) smoothed at the large scale, the luminance distribution acquiring unit 131 generates a luminance profile Spri1 (704 in FIG. 7, i=0, 1, 2, . . . , N) along a line segment perpendicular to the vessel center line.

The approximate feature identifying unit 1331 searches luminance values on the luminance profile Spri1 (704 in FIG. 7) to acquire a minimum value Gmin and a maximum value Gmax on the left and right sides, respectively, of a center line position G0, thereby identifying approximate wall position candidates.
(Step S540)

The wall feature identifying unit 1332 identifies vascular wall boundary positions in the following procedure.

(i) At each position on the vessel center line in the split detector image smoothed at the small scale in (i) of step S530, a luminance profile Spri2 (705 in FIG. 7) is acquired on a line segment substantially perpendicular to the vessel center line. Also, the approximate wall positions identified in (v) of step S530 are acquired.

(ii) On the luminance profile acquired in (i), two local maximum points near the approximate wall position on the right side and two local minimum points near the approximate wall position on the left side are detected, and the detected points are defined as wall boundary candidate points. The detected wall boundary candidate points are grouped into four groups: an outer boundary of the left wall, an inner boundary of the left wall, an outer boundary of the right wall, and an inner boundary of the right wall. Then, the first-order moment (i.e., "distance from the center line"× "luminance value") is calculated for each wall boundary candidate point. Here, a luminance value in the non-confocal image (i.e., L channel image for the boundary candidate of the left wall, and R channel image for the boundary candidate of the right wall) is referenced as the luminance value. A predetermined percentage of the moment values at the top and bottom in each group are considered as outliers, and the wall boundary candidate points having the outliers are removed. Then, the remaining wall boundary candidate points are interpolated in the wall running direction to identify the wall boundary. Any known technique may be used to determine the outliers.

Figure 11B:
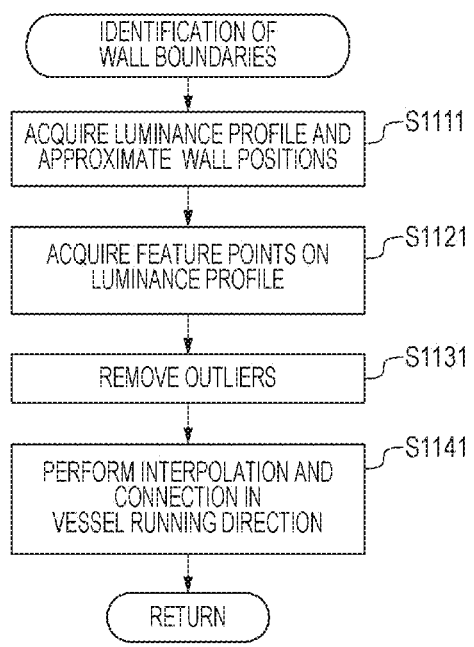

Details of the operation performed in step S540 of FIG. 5A will be described with reference to FIG. 7 and the flowchart of FIG. 11B. Note that step S1141 will not be described here, as it is the same as the corresponding step in the first embodiment.

(Step S1111)

At each position on the vessel center line in the split detector image smoothed at the small scale, a luminance profile Spri2 (705 in FIG. 7, i=0, 1, 2, . . . , N) along a line segment perpendicular to the vessel center line and approximate wall positions Gmin and Gmax are acquired.

(Step S1121)

In the luminance profile Spri2 acquired in step S1111, the wall feature identifying unit 1332 selects two local minimum values near the approximate wall position Gmin and two local maximum values near the approximate wall position Gmax to identify wall boundary candidate positions.

(Step S1131)

The image processor 130 groups the wall boundary candidates identified on the luminance profiles in step S1121 into the following four groups:

(i) outer boundary candidate group for the left wall,
(ii) inner boundary candidate group for the left wall,
(iii) outer boundary candidate group for the right wall, and
(iv) inner boundary candidate group for the right wall.

Then, the image processor 130 determines outliers in each boundary candidate group and removes them. In the present embodiment, the first-order moment (i.e., "luminance value"דdistance from the vessel center line") is calculated for each boundary candidate group. Then, a top Tt2% and a bottom Tb2% are considered as outliers, and wall boundary candidates having the corresponding moment values are removed. Here, a luminance value in the non-confocal image (i.e., L channel image for boundary candidates for the left wall, and R channel image for boundary candidates for the right wall) is referenced as the luminance value.

The present embodiment generates a smoothed and differentiated image by performing a subtraction operation between different types of non-confocal images smoothed at the same scale, but the present invention is not limited to this. For example, the present invention also includes the case of generating a smoothed and differentiated image by smoothing, at different scales, a split detector image generated by performing a subtraction operation between different types of non-confocal images.

The present embodiment deals with the case in which, when a moving image obtained after registration is smoothed at different scales, the smoothing is performed with different filter sizes after frame averaging. However, the present invention is not limited to this. For example, the present invention also includes the case in which an image obtained by frame averaging alone is used as an image smoothed at a small scale, and an image obtained by in-plane smoothing after frame averaging is used as an image smoothed at a large scale. The present invention also includes the case in which two-dimensional images smoothed at different scales are generated by applying a three-dimensional smoothing filter having different filter sizes in the in-plane direction to a moving image obtained after inter-frame registration. In the case of performing frame averaging, frames corresponding to a specific phase of a pulse wave may be selected and averaged, so as to prevent the positions of membrane boundaries forming the vascular wall from being changed by the impact of cardiac beats.

Although the present embodiment deals with the case of automatically acquiring a vessel center line using a morphological filter, the present invention is not limited to this. For example, the present invention also includes the case of manually setting a vessel center line by acquiring, from the instruction acquiring unit 140, the position of the vessel center line specified by the operator using the keyboard 306 or the mouse 307.

With the configuration described above, the image processing apparatus 10 captures a retinal vascular wall image using an SLO apparatus configured to acquire different types of non-confocal images, and generates a split detector image smoothed at a large scale and a split detector image smoothed at a small scale. The image processing apparatus 10 identifies wall boundaries on the basis of feature points on luminance profiles acquired, in a direction crossing the retinal vessel, in the split detector image smoothed at the large scale and the split detector image smoothed at the small scale.

Thus, a vascular wall region can be easily and robustly identified in an image of the subject's eye.

Third Embodiment

In images obtained by smoothing each retinal vascular wall image at different scales and differentiating the resulting images, the retinal vascular wall image being captured by an SLO apparatus configured to acquire a plurality of types of non-confocal images, an image processing apparatus according to the present embodiment identifies membrane boundaries of the vessel on the basis of feature points on luminance profiles acquired in a direction crossing the vessel.

Specifically, non-confocal images (R channel image and L channel image) of a retinal vascular wall captured using the SLO apparatus configured to simultaneously acquire confocal and non-confocal images are smoothed at two different scales and differentiated. In the image smoothed at a large scale and differentiated, the approximate position of the wall is identified from feature points on a luminance profile crossing the retinal vessel. In the image smoothed at a small scale and differentiated, membrane boundary candidate points are acquired from feature points on a luminance profile crossing the retinal vessel. After removal of outliers, the remaining membrane boundary candidate points are connected in the vessel running direction to identify the vessel membrane boundaries and measure the vessel membrane thickness.

The configuration of devices connected to the image processing apparatus 10 according to the present embodiment will not be described here, as it is the same as that in the first embodiment.

FIG. 12 illustrates functional blocks of the image processing apparatus 10 according to the present embodiment. The present embodiment differs from the first embodiment in that the image processor 130 includes a membrane feature identifying unit 1333 instead of the wall feature identifying unit 1332.

Figure 5B:
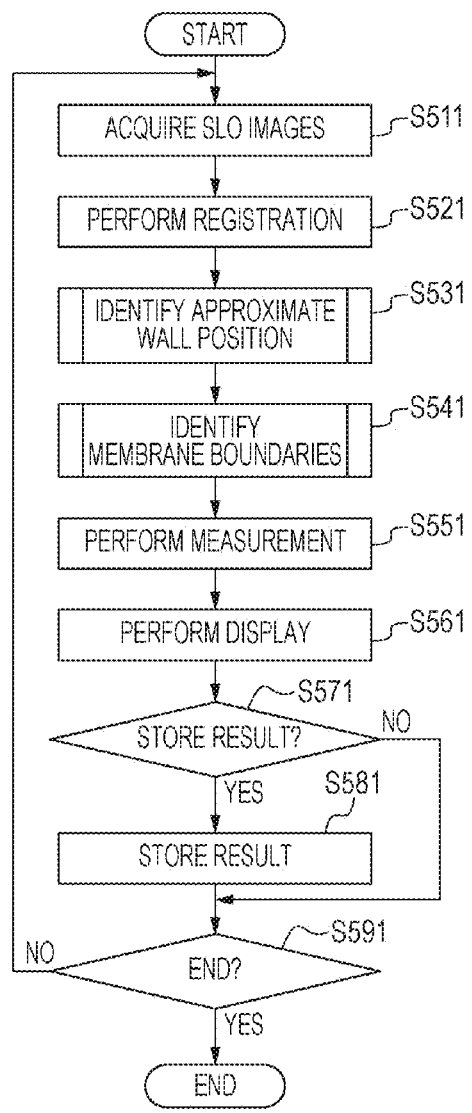

The image processing flow of the present embodiment is as illustrated in FIG. 5B, and steps other than steps S531, S541, S551, and S561 will not be described as they are the same as the corresponding steps in the first embodiment.

(Step S531)

The approximate feature identifying unit 1331 identifies the approximate position of each vascular wall in the following procedure.

(i) After frame averaging of the non-confocal images obtained after the inter-frame registration in step S521, the resulting image is smoothed at two different scales and the smoothed images are differentiated.

(ii) Of the images smoothed in (i), the non-confocal image smoothed at a small scale is subjected to a morphological filter to detect the center line of the retinal vessel.

(iii) At each position on the vessel center line in the image differentiated after being smoothed at a large scale in (i), a luminance profile is acquired on a line segment substantially perpendicular to the vessel center line.

(iv) On the luminance profile generated in (iii), the maximum value is detected in the rightward direction in the case of the R channel image and the minimum value is detected in the leftward direction in the case of the L channel image, so as to identify the approximate position of each wall. After grouping the approximate position candidate points for each of the left and right walls, the distances from the approximate position candidate points of each wall to the vessel center line are calculated. A predetermined percentage of the distance values at the top and bottom in each group are considered as outliers, and the approximate position candidate points having the outliers are removed. Then, the remaining approximate position candidate points of each wall are interpolated in the wall running direction. Any known technique may be used to determine the outliers.

Figure 13A:
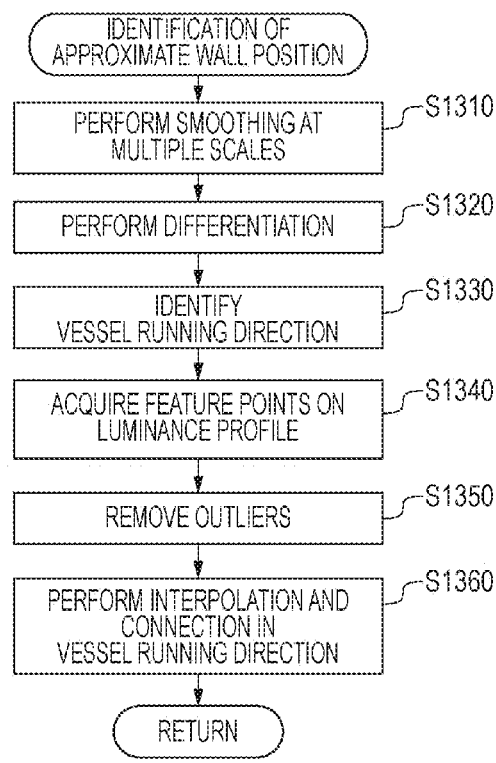

Details of the operation performed in step S531 of FIG. 5B will be described with reference to FIG. 7 and the flowchart of FIG. 13A. Note that steps S1330, S1350, and S1360 will not be described here, as they are the same as the corresponding steps in the first embodiment.

(Step S1310)

The smoothing and differentiating unit 132 performs smoothing, at multiple scales, on the non-confocal moving images (R channel image and L channel image) obtained after the inter-frame registration. Any known smoothing operation is applicable here. In the present embodiment, after frame averaging of the non-confocal images Dnr and Dnl obtained after inter-frame registration, the resulting image is subjected to a mean filter with filter sizes of 4 and 10.

(Step S1320)

The smoothing and differentiating unit 132 performs differentiation on the R channel image and the L channel image smoothed in step S1310 to generate smoothed and differentiated images. Although any known differentiating operation is applicable, a differential edge detection operator is used in the present embodiment.

(Step S1340)

Figure 6K:
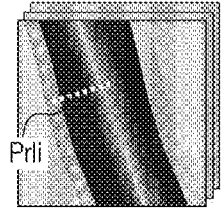
Figure 6L:
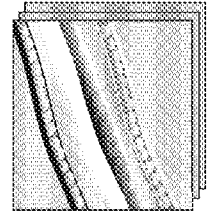
Figure 6M:
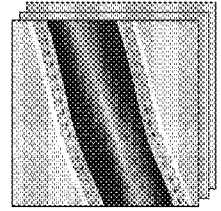

At each position on the vessel center line in the R channel image and the L channel image differentiated after being smoothed at the large scale, the luminance distribution acquiring unit 131 generates a luminance profile along a line segment perpendicular to the vessel center line. FIG. 6K illustrates a luminance profile generation position Prli (i=0, 1, 2, . . . , N) in the L channel image. A luminance profile generated at the corresponding position in the L channel image smoothed at the large scale and differentiated is shown in 706 of FIG. 7.

The approximate feature identifying unit 1331 searches luminance values from the center line position G0 on the luminance profile in the R channel image or L channel image differentiated after being smoothed at the large scale, and identifies approximate wall position candidates in the following manner. That is, the approximate feature identifying unit 1331 identifies approximate wall position candidates by acquiring a maximum value Gmax in the R channel image and a minimum value Gmin in the L channel image. A luminance profile Gprli1 in the L channel image smoothed at the large scale and differentiated is illustrated in 706 of FIG. 7. The luminance profile Gprli1 is referenced to identify approximate position candidates for the left wall.

(Step S541)

The membrane feature identifying unit 1333 identifies membrane boundaries in the following procedure.

(i) At each position on the vessel center line in the image differentiated after being smoothed at the small scale in (i) of step S531, a luminance profile is acquired on a line segment substantially perpendicular to the vessel center line. Also, the approximate wall positions identified in (iv) of step S531 are acquired.

(ii) On the luminance profile acquired in (i), three local maximum points near the approximate wall position on the right side and three local minimum points near the approximate wall position on the left side are detected, and the detected points are defined as membrane boundary candidate points. Then, after grouping the membrane boundary candidate points into six groups, the first-order moment (i.e., "distance from the center line"×"luminance value") is calculated for each membrane boundary candidate point. Here, a luminance value in the R channel image is reference as the luminance value of the membrane boundary candidate for the right wall, and a luminance value in the L channel image is reference as the luminance value of the membrane boundary candidate for the left wall. A predetermined percentage of the moment values at the top and bottom in each group are considered as outliers, and the membrane boundary candidate points having the outliers are removed. Then, the remaining membrane boundary candidate points are interpolated in the wall running direction to identify the membrane boundary. Any known technique may be used to determine the outliers.

Figure 13B:
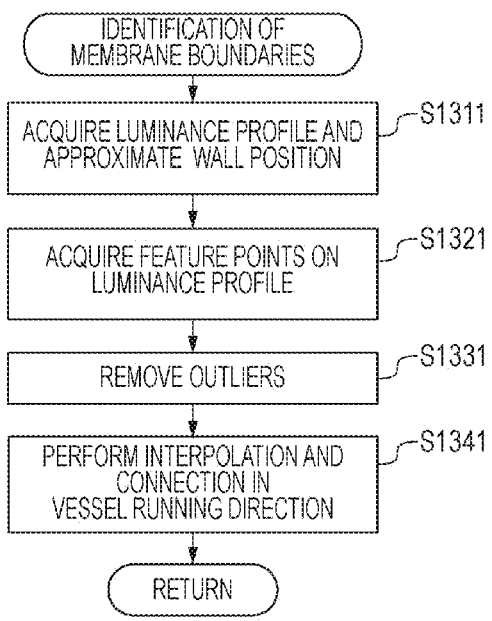

Details of the operation performed in step S541 of FIG. 5B will be described with reference to FIG. 7 and the flowchart of FIG. 13B. Note that step S1341 will not be described here, as it is the same as the corresponding step in the first embodiment.

(Step S1311)

At each position on the vessel center line in the image differentiated after being smoothed at the small scale, a luminance profile along a line segment perpendicular to the vessel center line and an approximate wall position are acquired. A luminance profile Gprli2 (i=0, 1, 2, . . . , N) in the L channel image smoothed at the small scale and differentiated is illustrated in 707 of FIG. 7.

(Step S1321)

In the luminance profile acquired in step S1311, the membrane feature identifying unit 1333 select three extremal points near the approximate wall position to identify membrane boundary candidate positions. For example, in the case of the L channel image, in the luminance profile Gprli2 shown in 707 of FIG. 7, the membrane feature identifying unit 1333 selects three local minimum values (Glmin_in, Glmin_out, and a small local minimum value between them) near the approximate wall position Gmin to identify membrane boundary candidate positions. For example, in the case of an artery having a vessel diameter of about 100 μm, a region from Glmin_in to the small local minimum point corresponds to an intima, and a region from the small local minimum point to Glmin_out corresponds to a media. In this case, Glmin_in is an inner boundary candidate for the intima of the left wall, the small local minimum point is a boundary candidate for the boundary between the intima and a membrane having wall cells of the left wall, and Glmin_out is an outer boundary candidate for the membrane having wall cells of the left wall.

(Step S1331)

The image processor 130 groups the membrane boundary candidates identified on the luminance profiles in step S1321 into the following six groups:

(i) outer boundary candidate group for the membrane having wall cells of the left wall, (ii) boundary candidate group for the boundary between the intima and the membrane having wall cells of the left wall, (iii) inner boundary candidate group for the intima of the left wall, (iv) outer boundary candidate group for the membrane having wall cells of the right wall, (v) boundary candidate group for the boundary between the intima and the membrane having wall cells of the right wall, and (vi) inner boundary candidate group for the intima of the right wall.

Then, the image processor 130 determines outliers in each boundary candidate group and removes them. In the present embodiment, the first-order moment (i.e., "luminance value"×"distance from the vessel center line") is calculated for each boundary candidate group. Then, a top Tt2% and a bottom Tb2% are considered as outliers, and membrane boundary candidates having the corresponding moment values are removed. Here, a luminance value in the non-confocal image (i.e., R channel image for membrane boundary candidates for the right wall, and L channel image for membrane boundary candidates for the left wall) is referenced as the luminance value.

(Step S551)

On the basis of the positions of the membrane boundaries forming each vascular wall identified in step S541, the measuring unit 135 measures the distribution of wall thickness or membrane thickness along the running of the vessel, and the distribution of index value related to the wall thickness or membrane thickness.

In the present embodiment, the measuring unit 135 calculates the wall thickness of the detected wall, the inner and outer diameters of the vessel, the index value (wall-to-lumen ratio) related to the wall thickness, the intima thickness, and the media thickness, and then determines the average value, standard deviation, and maximum and minimum values. These statistical values may be calculated not only for the entire image, but also for each branch vessel. The wall thickness and the membrane thickness may be calculated for each side (i.e., right or left side in the vessel running direction) within the branch vessel, or may be calculated for each small region.

(Step S561)

The display control unit 136 displays the acquired images, the positions of detected membrane boundaries, and the measurement result (wall and membrane thicknesses, and index values related to the wall and membrane thicknesses) on the monitor 305. In the present embodiment, the display control unit 136 displays the following (i) to (iv) on the monitor 305:

(i) non-confocal moving image (I1 in FIG. 9A),
image obtained by selecting frames corresponding to a specific phase of a pulse wave and averaging the frames (I2 in FIG. 9A), and
image extracting the lumen of the vessel for comparison (I3 in FIG. 9A);

(ii) detected membrane boundary positions;

(iii) graph showing the wall and membrane thicknesses measured along the running of the vascular wall or the index values related to the wall and membrane thicknesses; and (iv) map showing the distribution of the wall and membrane thicknesses calculated for each small region or the index values related to the wall and membrane thicknesses.

For (iv), the display control unit 136 associates the calculated values with a color bar and displays them in color.

For smoothing and differentiating a luminance profile, the present embodiment applies a smoothing filter and a differentiating filter to a non-confocal image to acquire a luminance profile on the smoothed and differentiated image. However, the present invention is not limited to this. For example, in the procedures illustrated in FIGS. 13C and 13D, a luminance profile is acquired in a direction crossing a vessel in a non-confocal image. The present invention also includes the case of generating a smoothed and differentiated luminance profile by repeating the process which involves linearly approximating the luminance profile in each small window and outputting the slope of the regression line while moving the small window at regular intervals.

In the present embodiment, two types of non-confocal images are each smoothed at different scales and differentiated, so as to identify the approximate wall positions and the membrane boundaries on the basis of feature points on the luminance profiles in images obtained by smoothing the L channel image (for the left wall) and the R channel image (for the right wall) at different scales and differentiating the resulting images. However, the present invention is not limited to this. For example, the present invention also includes the case of identifying the approximate positions of vascular walls and the membrane boundaries in the following manner. That is, the present invention also includes the case of identifying the approximate positions of vascular walls and the membrane boundaries by referring to luminance profiles in images obtained by smoothing a single non-confocal image (R+L image or image captured with a large pinhole diameter), such as that shown in FIG. 6M, at different scales and differentiating the resulting images.

The present embodiment deals with the case in which, when a moving image obtained after registration is smoothed at different scales, the smoothing is performed with different filter sizes after frame averaging. However, the present invention is not limited to this. For example, the present invention also includes the case in which an image obtained by frame averaging alone is used as an image smoothed at a small scale, and an image obtained by in-plane smoothing after frame averaging is used as an image smoothed at a large scale. The present invention also includes the case in which two-dimensional images smoothed at different scales are generated by applying a three-dimensional smoothing filter having different filter sizes in the in-plane direction to a moving image obtained after inter-frame registration. In the case of performing frame averaging, frames corresponding to a specific phase of a pulse wave may be selected and averaged, so as to prevent the positions of membrane boundaries forming the vascular wall from being changed by the impact of cardiac beats.

Although the present embodiment deals with the case of automatically acquiring a vessel center line using a morphological filter, the present invention is not limited to this. For example, the present invention also includes the case of manually setting a vessel center line by acquiring, from the instruction acquiring unit 140, the position of the vessel center line specified by the operator using the keyboard 306 or the mouse 307.

With the configuration described above, in images obtained by smoothing a retinal vascular wall image at different scales and differentiating the resulting images, the retinal vascular wall image being captured using an SLO apparatus configured to acquire non-confocal images, the image processing apparatus 10 identifies membrane boundaries on the basis of feature points on luminance profiles acquired in a direction crossing the retinal vessel.

Thus, a membrane region forming a vascular wall can be easily and robustly identified in an image of the subject's eye.

Other Embodiments

Although the image acquiring section 110 includes both the confocal data acquiring unit 111 and the non-confocal data acquiring unit 112 in the embodiments described above, the image acquiring section 110 does not necessarily need to include the confocal data acquiring unit 111 as long as it is configured to acquire two or more types of non-confocal data.

Although the embodiments described above deal with the cases where approximate wall positions and wall boundaries are identified on the basis of feature points on smoothed and differentiated luminance profiles, the approximate wall positions and the wall boundaries may be identified on the basis of feature points on luminance profiles in images smoothed at different scales. A luminance profile Pri before smoothing is shown in 701 of FIG. 7. In 701 of FIG. 7, P0 corresponds to the vessel center, Pwl corresponds to the vascular wall on the left side, and Pwr corresponds to the vascular wall on the right side. For example, to identify an approximate wall position, luminance values are searched on the left side (or right side) of the local maximum point in the center of the luminance profile, and a position having a predetermined ratio with respect to the difference between the maximum and minimum values (or difference between the luminance value at the vessel center P0 and the minimum value) may be identified as the approximate wall position.

If a set scale value for smoothing is not appropriate for the image to be processed, the number of feature points on a luminance profile in the smoothed and differentiated image may be insufficient. Therefore, for identifying wall boundaries, if the number of points having extremal values in a luminance profile on an image smoothed at a small scale and differentiated is less than four, the scale for smoothing may be changed until the number of points having extremal values reaches four. In the case of identifying membrane boundaries, if the number of points having extremal values in a luminance profile on a smoothed and differentiated image is less than six, the scale for smoothing may be changed until the number of points having extremal values reaches six.

To facilitate identification of a vessel region (including a vessel center line and wall boundaries) to be measured, the image processing apparatus 10 may include a region-of-interest setting unit configured to set at least one region of interest within a predetermined range in an acquired fundus image. The field of view of the region of interest is set to a size of 0.5 mm by 0.5 mm or less so as to include only one vessel. The length of a line segment on which the luminance distribution acquiring unit 131 generates a luminance profile may be set to be substantially double the diameter of the vessel to be measured.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-136387 filed Jul. 7, 2015, which is hereby incorporated by reference herein in its entirety.

What is claimed is:

1. An image processing apparatus comprising:
a processing unit configured to perform, on a luminance distribution acquired in at least one direction crossing a vessel region in a fundus image of a subject's eye, a first smoothing operation with a first size and a second smoothing operation with a second size smaller than the first size;
a first identifying unit configured to identify a position of a vascular wall in the fundus image on the basis of the luminance distribution obtained by performing the first smoothing operation; and
a second identifying unit configured to identify positions of inner and outer boundaries of the vascular wall in the fundus image on the basis of the luminance distribution obtained by performing the second smoothing operation.

2. The image processing apparatus according to claim 1, wherein the processing unit performs a first differentiating operation which is differentiation on a luminance distribution obtained by performing a smoothing operation with a first filter size corresponding to the first size, and performs a second differentiating operation which is differentiation on a luminance distribution obtained by performing a smoothing operation with a second filter size corresponding to the second size;
the first identifying unit identifies, as the position of the vascular wall, a feature point in the luminance distribution obtained by performing the first differentiating operation; and
the second identifying unit identifies, as the positions of the inner and outer boundaries of the vascular wall, a plurality of feature points in the luminance distribution obtained by performing the second differentiating operation.

3. The image processing apparatus according to claim 1, wherein the processing unit performs, on the luminance distribution acquired in the direction crossing the vessel region in the fundus image, a first linear approximation with a first window size corresponding to the first size and a second linear approximation with a second window size corresponding to the second size;

the first identifying unit identifies, as the position of the vascular wall, a feature point in the luminance distribution obtained by performing the first linear approximation; and the second identifying unit identifies, as the positions of the inner and outer boundaries of the vascular wall, a plurality of feature points in the luminance distribution obtained by performing the second linear approximation.

4. The image processing apparatus according to claim 1, further comprising an image acquiring unit configured to acquire, as the fundus image, an image obtained by performing a subtraction or division operation between a plurality of types of non-confocal images obtained by receiving a plurality of light beams produced by splitting scattered light from the fundus of the subject's eye.

5. An image processing apparatus comprising:
a processing unit configured to perform, on a luminance distribution acquired in at least one direction crossing a vessel region in a fundus image of a subject's eye, a smoothing operation with a first size and a second size smaller than the first size;
a first identifying unit configured to identify, as positions of a first vascular wall and a second vascular wall, a plurality of feature points in the luminance distribution obtained by performing the smoothing operation with the first size; and
a second identifying unit configured to identify, as positions of inner and outer boundaries of the first vascular wall and positions of inner and outer boundaries of the second vascular wall, a plurality of feature points near the identified positions of the first and second vascular walls in the luminance distribution obtained by performing the smoothing operation with the second size.

6. The image processing apparatus according to claim 5, wherein the second identifying unit identifies, as the positions of the inner and outer boundaries of the first vascular wall and the positions of the inner and outer boundaries of the second vascular wall, a plurality of extremal points near the positions of the first and second vascular walls in the luminance distribution obtained by performing the smoothing operation with the second size.

7. The image processing apparatus according to claim 5, wherein the second identifying unit identifies a plurality of feature points in the luminance distribution obtained by performing the smoothing operation with the second size, as a position of an inner boundary of an intima, a position of a boundary between the intima and a membrane having wall cells, and a position of an outer boundary of the membrane having wall cells for each of the first and second vascular walls.

8. The image processing apparatus according to claim 7, further comprising a measuring unit configured to measure at least one of a vessel membrane thickness, a vascular wall thickness, a vessel inner diameter, and a vessel outer diameter on the basis of at least one of the inner boundary of the intima, the boundary between the intima and the membrane having wall cells, and the outer boundary of the membrane having wall cells.

9. The image processing apparatus according to claim 5, further comprising a measuring unit configured to measure at least one of a vascular wall thickness, a vessel inner diameter, and a vessel outer diameter using the positions of the outer and inner boundaries of the first vascular wall and the positions of the outer and inner boundaries of the second vascular wall.

10. The image processing apparatus according to claim 5, further comprising a region-of-interest setting unit configured to set at least one region of interest with a size of 0.5 mm by 0.5 mm or less in the fundus image to identify the vessel region in the fundus image.

11. The image processing apparatus according to claim 5, further comprising an image acquiring unit configured to acquire, as the fundus image, an R channel image and an L channel image which are a plurality of types of non-confocal images obtained by receiving a plurality of light beams produced by splitting scattered light from the fundus of the subject's eye, wherein the second identifying unit identifies the positions of the inner and outer boundaries of the first vascular wall using one of the R channel image and the L channel image, and identifies the positions of the inner and outer boundaries of the second vascular wall using the other of the R channel image and the L channel image.

12. An image processing apparatus comprising:
a first identifying unit configured to identify a position of a vascular wall in a fundus image of a subject's eye on the basis of a luminance distribution acquired in at least one direction crossing a vessel region in the fundus image; and
a second identifying unit configured to identify a plurality of feature points near the identified position of the vascular wall in the luminance distribution as positions of inner and outer boundaries of the vascular wall in the fundus image.

13. An image processing method comprising:
a processing step of performing, on a luminance distribution acquired in at least one direction crossing a vessel region in a fundus image of a subject's eye, a first smoothing operation with a first size and a second smoothing operation with a second size smaller than the first size;
a first identifying step of identifying a position of a vascular wall in the fundus image on the basis of the luminance distribution obtained by performing the first smoothing operation; and
a second identifying step of identifying positions of inner and outer boundaries of the vascular wall in the fundus image on the basis of the luminance distribution obtained by performing the second smoothing operation.

14. A non-transitory computer-readable storage medium storing a program causing a computer to execute each step of the image forming method according to claim 13.

15. An image processing method comprising:
a processing step of performing, on a luminance distribution acquired in at least one direction crossing a vessel region in a fundus image of a subject's eye, a smoothing operation with a first size and a second size smaller than the first size;
a first identifying step of identifying, as positions of a first vascular wall and a second vascular wall, a plurality of feature points in the luminance distribution obtained by performing the smoothing operation with the first size; and a second identifying step of identifying, as positions of inner and outer boundaries of the first vascular wall and positions of inner and outer boundaries of the second vascular wall, a plurality of feature points near the identified positions of the first and second vascular walls in the luminance distribution obtained by performing the smoothing operation with the second size.

16. A non-transitory computer-readable storage medium storing a program causing a computer to execute each step of the image forming method according to claim 15.

17. An image processing method comprising:
   a first identifying step of identifying a position of a vascular wall in a fundus image of a subject's eye on the basis of a luminance distribution acquired in at least one direction crossing a vessel region in the fundus image; and
   a second identifying step of identifying a plurality of feature points near the identified position of the vascular wall in the luminance distribution as positions of inner and outer boundaries of the vascular wall in the fundus image.

18. A non-transitory computer-readable storage medium storing a program causing a computer to execute each step of the image forming method according to claim 17.

* * * * *